US006168913B1

(12) United States Patent
Hochlowski et al.

(10) Patent No.: US 6,168,913 B1
(45) Date of Patent: *Jan. 2, 2001

(54) CODING COMBINATORIAL LIBRARIES WITH FLUORINE TAGS

(75) Inventors: Jill Edie Hochlowski, Green Oaks; Thomas J. Sowin, Wadsworth; Daniel W. Norbeck, Crystal Lake; Warren S. Wade, Grayslake; David N. Whittern, Green Oaks, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/949,987

(22) Filed: Oct. 14, 1997

(51) Int. Cl.$^7$ .......................... C12Q 1/00; G01N 33/566; G01N 33/543
(52) U.S. Cl. .................... 435/4; 435/6; 435/7.1; 436/501; 436/518; 548/69; 554/103; 554/213; 562/400; 562/426; 562/433; 562/456; 562/490; 562/493; 568/663
(58) Field of Search ..................... 435/4, 4.1, 7.1, DIG. 46; 436/501, 518; 562/400, 426, 433, 456, 493, 490, 496; 554/103, 213; 568/663; 585/24, 6; 548/469

(56) References Cited

U.S. PATENT DOCUMENTS

| 5,565,324 | * | 10/1996 | Still et al. ............................ 435/6 |
| 5,635,598 | * | 6/1997 | Lebl et al. ......................... 530/334 |
| 5,708,153 | | 1/1998 | Dower et al. . |
| 5,840,485 | * | 11/1998 | Lebl et al. ............................ 435/6 |
| 5,846,839 | * | 12/1998 | Gallop et al. ...................... 436/518 |

FOREIGN PATENT DOCUMENTS

| 2304410 | 3/1997 | (GB) . |
| 9408051 | 4/1994 | (WO) . |

OTHER PUBLICATIONS

B. Yan et al., "Infrared Spectrum of a Single Resin Bead for Real–Time Monitoring of Solid–Phase Reactions", *J. Org. Chem.*, vol. 60, No. 17, (1995), pp. 5736–5738.
C. Chen et al., "Analogous' organic Synthesis of Small–Compound Libraries: Validation of Combinatorial Chemistry in Small–Molecule Synthesis", *J. Am. Chem. Soc.*, vol. 116, No. 6, (1994), pp. 2661–2662.
H. M. Geysen et al., "Isotope or Mass Encoding of Combinatorial Libraries", *Chemistry and Biology*, vol. 3, No. 8, (1996) pp. 679–688.
S. Brenner et al., "Encoded Combinatorial Chemistry", *Proc. Natl. Acad. Sci. USA*, vol. 89, (1992), pp. 5381–5383.

V. Nikolaiev et al., "Peptide–Encoding for Structure Determination of Nonsequenceable Polymers Within Libraries Synthesized and Tested on Solid–Phase Supports", *Peptide Research*, vol. 6, No. 3, (1993), pp. 161–170.
R. W. Armstrong et al., "Microchip Encoded Combinatorial Libraries: Generation of a Spatially Encoded Library from a Pool Synthesis", *Medicinal Chemistry*, vol. 50, No. 6, (1996), pp. 258–260.
A. Furka et al., "General Method for Rapid Synthesis of Multicomponent Peptide Mixtures", *Int. J. Peptide Res.*, vol. 37, (1991), pp. 487–493.
K. Russell et al., "Analytical Techniques for Combinatorial Chemistry: Quantitative Infrared Spectroscopic Measurements for Deuterium–Labeled Protecting Groups", *J. Am. Chem.*, vol. 118, (1996), pp. 7941–7945.
M. H. J. Ohlmeyer et al., "Complex Synthetic Chemical Libraries Indexed with Molecular Tags", *Proc. Natl. Acad. Sci. USA*, vol. 90, (1993), pp. 10922–10926.
E. J. Moran et al., "Radio Frequency Tag Encoded Combinatorial Library Method for the Discovery of Tripeptide–Substituted Cinnamic Acid Inhibitors of the Protein Tyrosine Phosphatase PTP1B", *J. Am. Chem. Soc.*, vol. 117, No. 43, (1995), pp. 10787–10788.
Z. J. Ni et al., "Versatile Approach to Encoding Combinatorial Organic Syntheses Using Chemically Robust Secondary Amine Tags", *J. Med. Chem.*, vol. 39, (1996), pp. 1601–1608.
A. Borchardt et al., "Synthetic Receptor Binding Elucidated with an Encoded Combinatorial Library", *J. Am. Chem. Soc.*, vol. 116, (1994), pp. 373–374.
J. J. Baldwin et al., "Synthesis of a Small Molecule Combinatorial Library Encoded with Molecular Tags", *J. Am. Chem. Soc.*, vol. 117, (1995), pp. 5588–5589.
J. M. Kerr et al., "Encoded Combinatorail Peptide Libraries Containg Non–Natural Amino Acids", J. Am. Chem. Soc., vol. 115, (1993), pp. 2529–2531.
H. P. Nestler et al., "A General Method for Molecular Tagging of Encoded Combinatorial Chemistry Libraires", *J. Org. Chem.*, vol. 59, No. 17, (1994), pp. 4723–4724.
K. C. Nicolaou et al., "Radiofrequency Encoded Combinatorial Chemistry", *Angew. Chem. Int. Ed. Engl.*, vol. 34, No. 20, (1995), pp. 2289–2291.3q.

* cited by examiner

Primary Examiner—Jyothsna Venkat
Assistant Examiner—Joseph W. Ricigliano
(74) Attorney, Agent, or Firm—Daniel W. Collins

(57) ABSTRACT

The present invention relates to coding combinatorial chemical libraries synthesized on a plurality of solid supports by attaching "tags" that comprise fluorine containing compounds in combinations and/or ratios. The tags can be decoded while attached to the solid support by fluorine nuclear magnetic resonance spectroscopy to follow the reaction history of individual beads, and to determine the particular member of the library that is attached on the bead.

3 Claims, 15 Drawing Sheets

CODING COMBINATORIAL LIBRARIES WITH FLUORINE TAGS

TECHNICAL FIELD OF THE INVENTION

The present invention relates to a process of coding and identifying individual members of a combinatorial chemical library synthesized on a plurality of solid supports. The process provides for attaching fluorine containing tags to solid supports that is later decoded by fluorine nuclear magnetic resonance spectroscopy.

BACKGROUND OF THE INVENTION

Mix and split combinatorial chemistry is a synthetic tool that provides libraries of numerous compounds that are structurally related. With this method, the libraries are constructed on a solid support by assembling sets of chemically reactive building blocks (hereinafter "units" or "monomers") in many possible combinations.

To understand the mix and split method, one should first understand its predecessor, solid phase peptide synthesis. In solid phase peptide synthesis, one set of solid supports (e.g., beads) having reactive functionalities is reacted with an amino acid, followed by another amino acid, and so on. Once the desired polypeptide is formed, one can cleave the peptide from the bead. Thus, for example, if one reacts amino acids A, B and C in that sequence, one can form an ABC tripeptide. Further, one can also react amino acids A, B and C in five other sequences, ACB, BAC, BCA, CAB and CBA. If one were to allow duplication of each amino acid, for example AAA, one could generate up to 27 tripeptides by this method. One drawback to this method is that each tripeptide is individually synthesized, so that 27 syntheses are required to make all permutations of tripeptides made from amino acids A, B and C. On the other hand, at the end of each synthesis, one either has a pretty good idea of which tripeptide was made, or can easily cleave the product off of the bead and identify the compound by traditional analytical methods.

The mix and split method improves on its predecessor by simultaneously adding different monomers to a mixture of beads that already carry various units. Using the A, B and C amino acids as an example, three different pools of beads are reacted with A, B or C, respectively, and then mixed together. Thus, a third of this mixture are beads carrying A, a third are beads carrying B and a third are beads carrying C. This mixture is then split into three pools. Each pool is reacted with A, B or C, respectively. Thus, one pool will contain beads that carry one of AA, BA or CA, another will contain beads that carry one of AB, BB or CB, and the third will contain beads that carry one of AC, BC or CC. The three pools are then mixed together again and split again into three pools and reacted with A, B or C, respectively. Thus, one pool will now carry one of AAA, BAA, CAA, ABA, BBA, CBA, ACA, BCA or CCA, another will now carry one of AAB, BAB, CAB, ABB, BBB, CBB, ACB, BCB or CCB, and the third will now carry one of AAC, BAC, CAC, ABC, BBC, CBC, ACC, BCC or CCC. In nine reactions, the mix and split method generates all 27 tripeptide permutations from A, B and C.

Moreover, the mix and split method is no longer limited to peptide synthesis. Many different chemical units and many different types of reactions can now be used to form libraries of many different classes of compounds by mix and split combinatorial chemistry. Chemical units, both naturally-occurring and synthetic, can include compounds containing reactive functional groups such as nucleophiles, electrophiles, dienes, alkylating agents, acylating agents, diamines, nucleotides, amino acids, sugars, lipids or derivatives thereof, organic monomers, synthons, and combinations thereof. Alternatively, reactions can include alkylation, acylation, nitration, halogenation, oxidation, reduction, hydrolysis, substitution, elimination, addition, and the like. This method can produce non-oligomers, oligomers, or combinations thereof in extremely small amounts. Non-oligomers include a wide variety of organic molecules, e.g., heterocyclics, aromatics, alicyclics, aliphatics and combinations thereof, such as steroids, antibiotics, enzyme inhibitors, ligands, hormones, drugs, alkaloids, opioids, terpenes, porphyrins, toxins, catalysts, as well as combinations thereof. Oligomers include oligopeptides, oligonucleotides, oligosaccharides, polylipids, polyesters, polyamides, polyurethanes, polyethers, poly(phosphorus derivatives) e.g., phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom, for the most part, will be bonded to C, H, N, O and combinations thereof.

While the split and mix method can quickly generate a diverse number of compounds, this diversity also generates its greatest challenge—identifying individual compounds from the mixture. For example, if one picks up a bead from a mixture of beads carrying AAA, BAA, CAA, ABA, BBA, CBA, ACA, BCA or CCA, how does one determine which tripeptide is attached? Because each bead generally has only a small amount of product, the reaction history and composition of individual beads are hard to determine. In fact, the amounts of product on each bead are so small (depending on the size of the solid support, about 10 picomoles to 1 nanomole), and the structures on each bead are so similar (e.g., BAA vs. ABA), that traditional analysis such as proton or carbon nuclear magnetic resonance spectroscopy (NMR) and mass spectroscopy (MS) are generally insufficient for determining the compound structure on each bead.

Other attempts to analyze combinatorial constructs by tagging the solid support require that the tags be detached for analysis (See, e.g., International Patent Publication No. WO94/08051). However, detachment adds an extra reaction step to the overall construction, and the translation can become garbled during the process of detachment. Further, one still needs to have distinctive tags that are present on the bead in sufficient quantities for decoding.

Various synthetic techniques and strategies are important factors in determining the success of combinatorial chemistry and are well-known in the art. However, to optimize the power of the mix and split method as a synthetic tool, one must develop a method to readily identify the individual compounds attached to each bead of the generated compound libraries. In other words, one must be able to pick one bead from a library of many beads of many different compounds and easily identify the specific member of the library on that bead. U.S. patent application Ser. No. 08/717, 710, filed on Sep. 13, 1996 by Hochlowski et al. (pending), discloses that IR or Raman readable tags can be used to code combinatorial libraries without detaching the tag or the library for analysis. However, the CombiChem industry continues to seek alternative coding schemes to expand the utility of the process.

BRIEF SUMMARY OF THE INVENTION

The present invention relates to coding Combinatorial Chemistry libraries synthesized on a plurality of solid supports by attaching "tags" that comprise fluorine containing compounds. The codes are created by varying singular tags, combining different tags and/or varying the ratio of different combinations of tags. By applying appropriate tags at particular stages of the synthesis of a combinatorial library, one can later determine which compound was made on a particular bead by fluorine nuclear magnetic resonance spectroscopy (FNMR).

Coding combinatorial libraries with fluorine tags has many advantages over the prior art. For the most part, fluorine is a robust moiety that is unaffected by the chemical reactions used to construct the library. Further, the fluorine tagged solid support can be read without detaching the tag from the solid support. In fact, this method does not require detachment of either the tag or the library member from the solid support to follow the reaction history of individual beads, or to determine the particular member of the library that is attached to the bead. In addition, the FNMR spectrum is distinctive enough to be read in small quantities, and the peak areas are quantitative so that coding by a ratio of tags can be accomplished.

DETAILED DESCRIPTION OF THE INVENTION

Definitions

Figure 1:
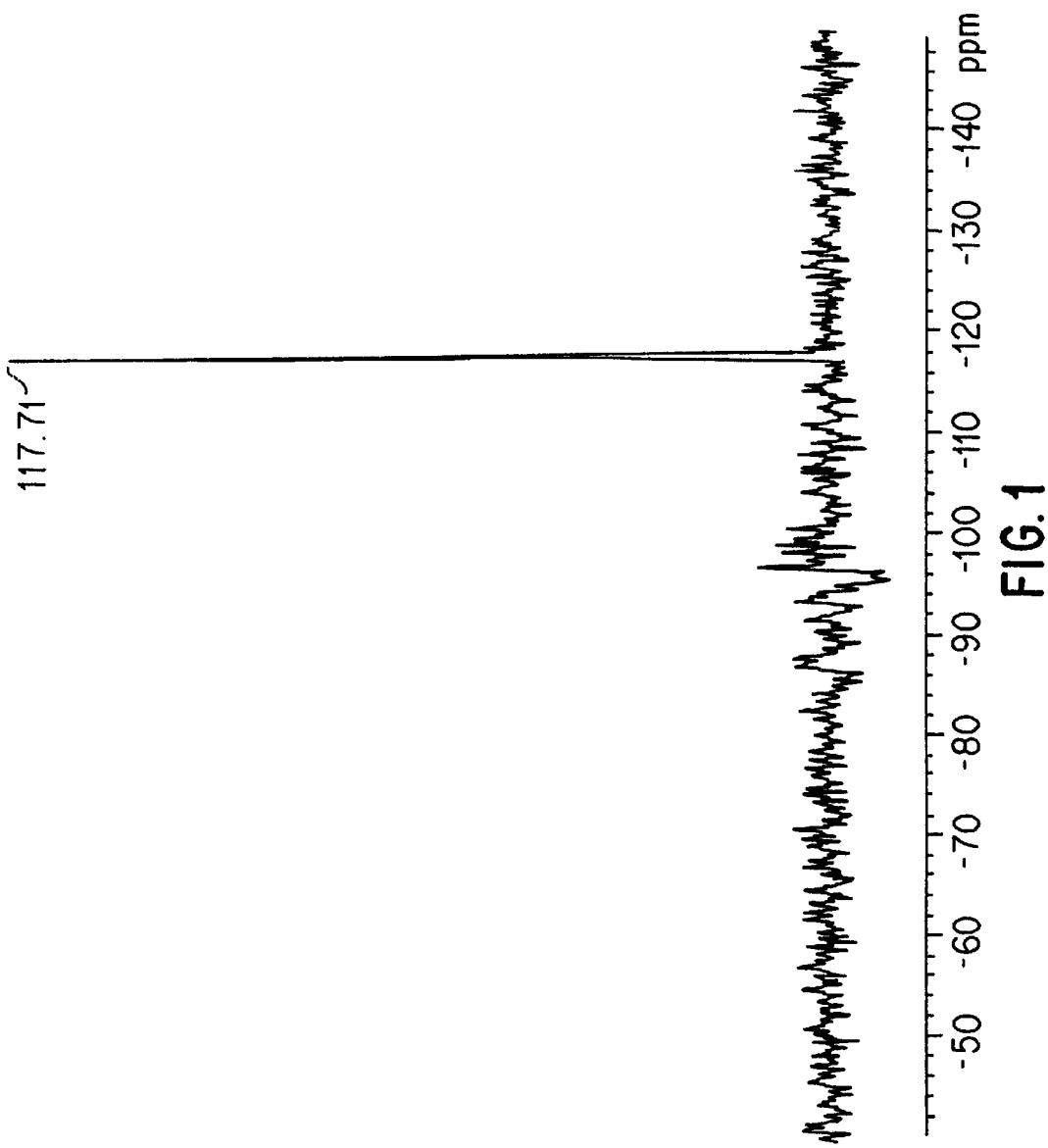
FIGS. 1–15 illustrate the FNMR spectra of various tags or combination of tags.

The term "resin" as used herein refers to resins of the type commonly used in the art of synthetic peptide preparation or in solid phase organic synthesis. Examples of such resins include, but are not limited to, methyl benzhydrylamine (MBHA) or benzhydrylamine (BHA) or Merrifield resin (i.e. chloromethylated polystyrene), Wang resin, Tentagel, Rink, etc.

Suitable protecting groups for amines include, but are not limited to, t-butyloxycarbonyl (BOC), benzyloxycarbonyl (Cbz), 9-fluorenylmethyloxycarbonyl (Fmoc), allyloxycarbonyl (Alloc), biphenyloxycarbonyl (Bpoc), 1-(4,4-dimethyl-2,6-dioxocyclohex-1-ylidene)ethyl (Dde) and triphenylmethyl (trityl).

Common solvents include, but are not limited to, N,N-dimethylformamide (DMF), 1,2-dimethoxyethane (DME), Dichloromethane (DCM), tetrahydrofuran (THF) and Dimethylacetamide (DMA).

Examples of common coupling agents for preparing amide bonds are: N,N'-dicyclohexylcarbodiimide (DCC), N,N'-diisopropylcarbodiimide (DIC), benzotriazol-1-yloxy-tris(dimethylamino)phosphonium-hexafluorophosphate (BOP), bis(2-oxo-3-oxazolidinyl)phosphine chloride (BOPCI), Bromo-tris-pyrrolidino-phosphonium hexafluoro-phosphate (PyBroP).

Other common abbreviations include: 4-dimethylaniinopyridine (DMAP), trifluoroacetic acid (TFA), triethylamine (TEA), diaminopropionic acid (DAP), tosylate (Ts), mesylate (Ms, by contrast to MS for mass spectroscopy), 2,2'-bis(diphenylphosphonyl)-1,1'-binaphthyl (BINAP), lysine (Lys), ornithine (Orn) and 2-ethoxy-1-ethoxycarbonyl-1,2-dihydroquinoline (EEDQ).

All citations herein are incorporated by reference.

As described above, mix and split combinatorial synthesis provides simultaneous construction of many structurally related compounds on solid supports (without being so limited, hereinafter "beads"). These sets of related compounds are called libraries. After a particular set of reactions, each bead holds multiple copies of individual chemical entities called members of the library. The present invention provides a process for determining the individual members of a Combinatorial Chemistry library on each bead. The process comprises covalently attaching to each of the plurality of beads a FNNMR detectable code. The code is one or a set of fluorine containing compounds that can provide an unique FNMR spectrum. The presence or absence of a specific tag, or the ratio of two or more tags on the bead identifies the unique chemical structure on the bead or the chemical steps used to generate that structure.

Solid Supports

Solid supports for use in Combinatorial Chemistry syntheses are well known in the art (See, e.g., International Patent Publication No. WO94/08051). A common solid support is a polystyrene bead. Depending upon the nature of the synthesis or the assay for the final product, a particular bead can be more or less desirable. While beads are especially convenient, other solid supports, such as glass capillaries, hollow fibers such as cotton, etc., are also useful. In some cases, the size of the solid support provides a desired variation in reaction histories. Any convenient composition can be used for the particles or beads. A composition's utility depends on whether it maintains its mechanical integrity during the various process stages, can be functionalized, has functional groups or allows for reaction with an active species, allows for serial synthesis as well as attachment of the identifiers, can be readily mixed and separated, and/or allows for convenient detachment of tags and products.

Exemplary beads used in this process include cellulose beads, pore-glass beads, silica gel, polystyrene beads (particularly those cross-linked with divinylbenzene), grafted copolymer beads such as polyethylene glycol/polystyrene, polyacrylamide beads, latex beads, dimethylacrylamide beads, particularly cross-linked with N,N'-bis-acryloyl ethylene diamine and comprising N-t-butoxycarbonyi-β-alanyl-N'-acryloyl hexamethylene diamine composites, such as glass particles coated with a hydrophobic polymer such as cross-linked polystyrene or a fluorinated ethylene polymer to which is grafted linear polystyrene; and the like. General reviews of useful solid supports (particles) that include a covalently-linked reactive functionality can be found in Atherton et al., Prospectives in Peptide Chemistry, Karger, 101–117 (1981); Amamath et al., Chem. Rev., 77:183–217 (1977); and Fridkin, The Peptides, Vol. 2, Chapter 3, Academic Press, Inc., (1979), pp. 333–363. Another preferred solid support is a polystyrene or polyethylene glycol resin. Such resins can be obtained from commercial sources (Wang, NovaSyn-PEG) or prepared in accordance with standard procedures well-known in the art. One procedure to prepare a Wang polystyrene resin is described in the Examples below.

Beads can be functionalized in a variety of ways to allow attachment of an initial reactant depending upon the nature of the syntheses. Functionalities present on the bead can include aldehyde, acid, ketone, hydroxy, aminohalide, amino, thio, active halogen (Cl or Br) or pseudohalogen (e.g. —CN, toluenesulfonyl, methanesulfonyl, bromosulfonyl, triflurosulfonyl or the like). In selecting the functionality, some consideration should be given to the fact that the tags will usually also become bound to the bead. Consideration will include whether the same or a different functionality should be associated with the product and the tag, as well as whether the two functionalities will be compatible with the product or tag attachment or detachment stages, as appropriate. Different linking groups can be employed for the product, so that a specific quantity of the product can be selectively released. In some instances the support can have protected functionalities which can be partially or wholly deprotected prior to each stage, and in the latter case reprotected. For example, an amino group can be protected with a carbobenzoxy group as in polypeptide synthesis, a hydroxy group with a benzyl ether, etc.

Tags

Tags used in accordance with a process of the present invention are any fluorine containing compound capable of covalent attachment to the solid support and can be readily detected by FNMR. Such compounds are well known in the art. Preferred tags include compounds that attach to a solid support by amide coupling of a carboxylic acid. In general, such a tag is attached on a site on the solid support that is different ("orthogonal" in Combinatorial Chemistry lingo) than the site where the combinatorial library is attached. Without limiting the scope of the invention, preferred tags with their distinctive FNMR chemical shifts are listed below as Tags 1–35.

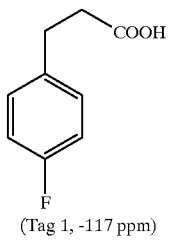

(Tag 1, -117 ppm)

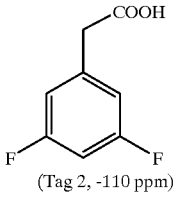

(Tag 2, -110 ppm)

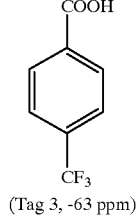

(Tag 3, -63 ppm)

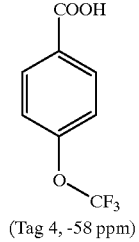

(Tag 4, -58 ppm)

(Tag 5, -113 ppm)

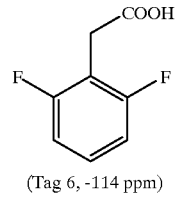

(Tag 6, -114 ppm)

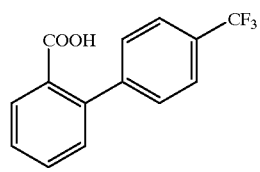

(Tag 7, -62 ppm)

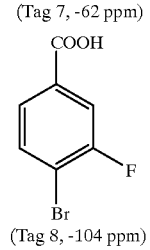

(Tag 8, -104 ppm)

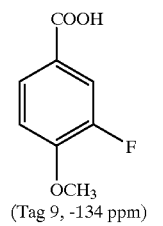

(Tag 9, -134 ppm)

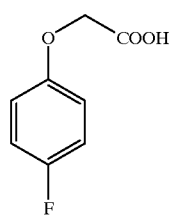

(Tag 10, -122 ppm)

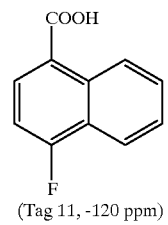

(Tag 11, -120 ppm)

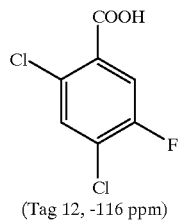

(Tag 12, -116 ppm)

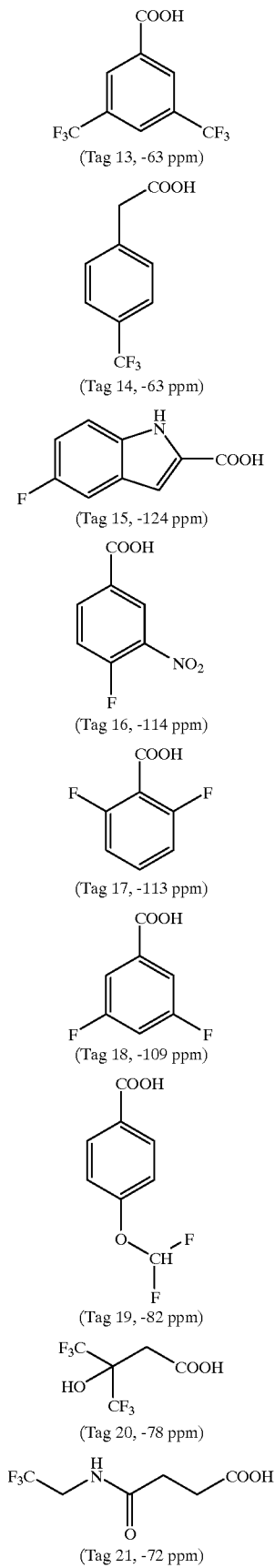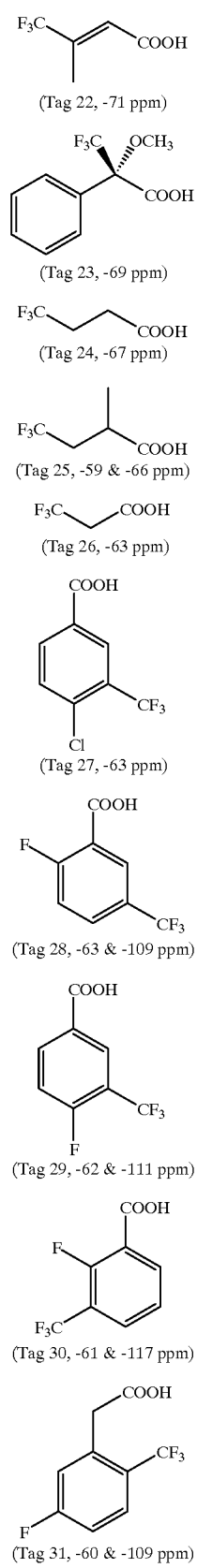

-continued

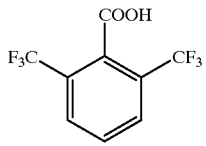
(Tag 32, -59 ppm)

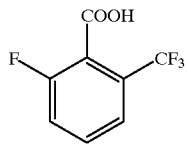
(Tag 33, -59 & -115 ppm)

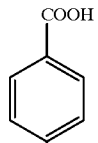
(Tag 34, -42 ppm)

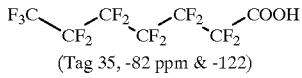
(Tag 35, -82 ppm & -122)

In order to expand the applicability of this methodology to the coding of smaller beads and/or lower loading resins, the intensity of the fluorine tags signal may be enhanced by the use of compounds containing multiple "NMR equivalent" fluorines. Tags 36–57 below provide additional examples of "loaded" tags.

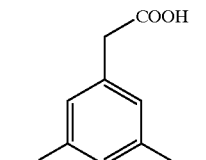
(Tag 36, -63 ppm)

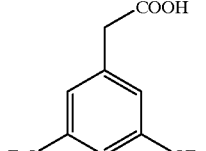
(Tag 37)

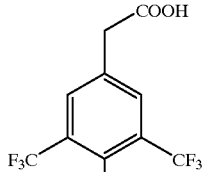
(Tag 38)

-continued

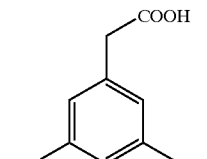
(Tag 39)

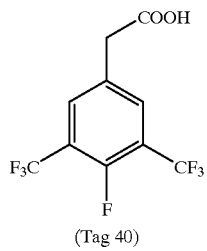
(Tag 40)

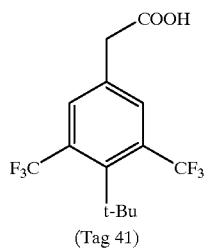
(Tag 41)

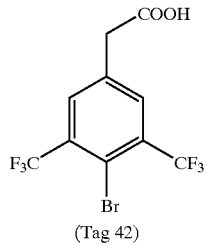
(Tag 42)

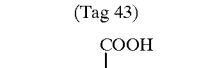
(Tag 43)

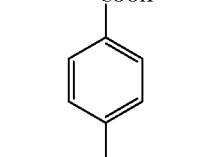
(Tag 44)

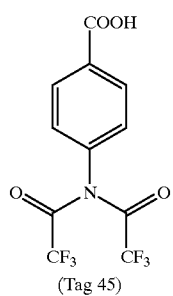
(Tag 45)
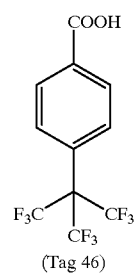
(Tag 46)
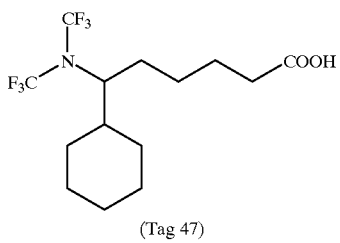
(Tag 47)
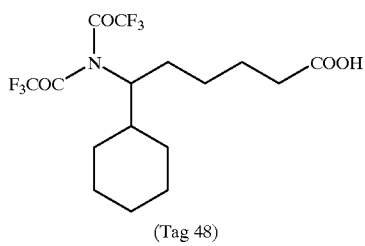
(Tag 48)
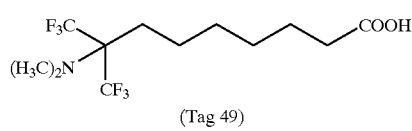
(Tag 49)
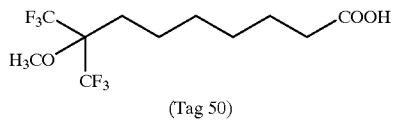
(Tag 50)
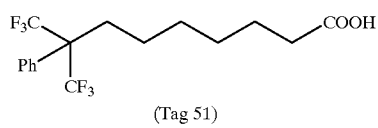
(Tag 51)
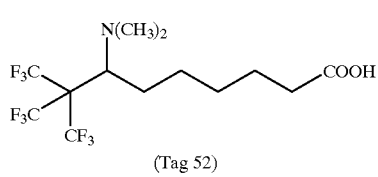
(Tag 52)
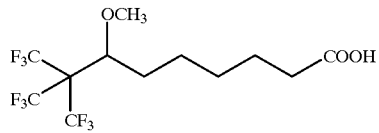
(Tag 53)
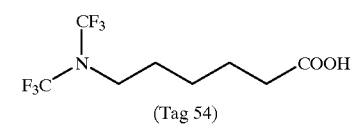
(Tag 54)
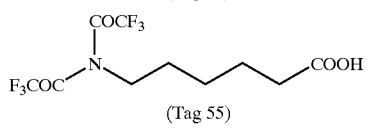
(Tag 55)
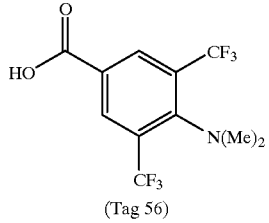
(Tag 56)
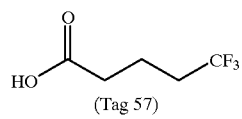
(Tag 57)
Additional preferred embodiments of tags include acetylene moieties that contain the fluorine atom.
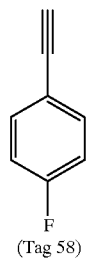
(Tag 58)
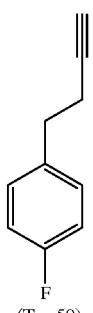
(Tag 59)
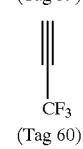
(Tag 60)

-continued

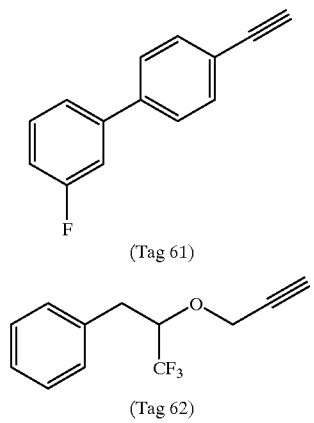

(Tag 61)

(Tag 62)

Other preferred embodiments of tags are shown in the schemes and examples described below.

Codes

One can code a synthetic sequence with individual tags, combinations of tags, or varying ratios of tag combinations. Table 1 provides examples of various codes, and demonstrates that one can generate infinite numbers of codes from very few tags by simply varying combinations or ratios. The ratio codes are created by simply mixing two or more tags together in the desired ratio and attaching the mixture of tags to the incipient combinatorial libraries. The ordinary artisan would know that although only one or two attachment sites are generally shown for each bead, each bead actually contains numerous attachment sites. Therefore, for a code based on a mixture of tags, each tag in the mixture will attach to the bead in a statistical distribution based, in part, on the ratio of tags in the mixture, and on the reactivity of the attaching functionalities.

TABLE 1

| Code | Tag(s) | Tag ratios |
|------|--------|------------|
| 1    | 1      | —          |
| 2    | 2      | —          |
| 3    | 3      | —          |
| 4    | 4      | —          |
| 5    | 1/2    | (1:1)      |
| 6    | 1/2    | (2:1)      |
| 7    | 1/2    | (1:2)      |
| 8    | 1/3    | (2:1)      |
| 9    | 1/3    | (3:1)      |
| 10   | 1/4    | (2:1)      |
| 11   | 1/4    | (3:1)      |
| 12   | 2/3    | (1:1)      |
| 13   | 2/3    | (2:1)      |
| 14   | 2/4    | (1:1)      |
| 15   | 2/4    | (2:1)      |
| 16   | 1/2/3  | (3:2:1)    |
| 17   | 1/2/4  | (3:2:1)    |
| 18   | 1/3/4  | (3:1:1)    |
| 19   | 2/3/4  | (3:2:2)    |
| 20   | 2/3/4  | (3:1:1)    |

The tags can also be used to generate a code by virtue of either their presence or abscence. For example, for a base 2 or binary system (M=2) with three identifiers (N=3), one can generate 8 ($MN^N=2^3$) codes. Further, as the number of identifiers increases the number of available codes increase exponentially (e.g., a binary system (M=2) with 4 identifiers (N=4) can generate up to 24 or 16 different codes). As an example of a binary code with three identifiers, one can choose tags 1–3 from above (Tag 1, –117 ppm; Tag 2, –0 ppm; Tag 3, –63 ppm). In the binary system, the eight codes available from the three tags are: 000, 100, 010, 001, 110, 101, 011 and 111, where the first position corresponds to tag 1, the second position corresponds to tag 2 and the third position corresponds to tag 3. Thus, if one were to pick up a bead having a –117 shift and a –63 shift, one can conclude that the bead corresponds to the 101 code. If one does not observe any FNMR shift, one must have a 000 code. Finally, if one found a –110 shift only, one must have a 010 coded bead.

As shown above, the present invention can generate complicated codes. However, such codes are not necessary because large numbers of fluorine containing compounds with distinct FNMR chemical shifts are readily available. In addition, one can generate large numbers of codes by simply making two-tag combinations with the available fluorine containing compounds. For example, assuming one cannot distinguish duplicate tags from singular tags, the three tags used in the binary example above can generate 6 codes: 1, 2, 3, 1/2, 1/3 and 2/3. With five tags, one can generate 15 codes by this method.

Attaching the Tags to the Beads

The precise means for covalently attaching the identifiers to the bead will depend, as is well-known in the art, on the chemical structure of the tag and the nature of the solid support. In a preferred embodiment, one can synthesize coded resin suitable for building Combinatorial Chemistry libraries by attaching a "code linker" such as, for example, a lysine having different protecting groups on each of its amines to a suitable solid support such as, for example, aminomethylpolystyrene, as shown in Scheme 1. As an aside, the term "orthogonal" in Combinatorial Chemistry lingo refers to differentiated functionalities on the same moiety. Thus, the lysine which has a different protecting group on each of its two amines is "orthogonally protected".

Scheme 1

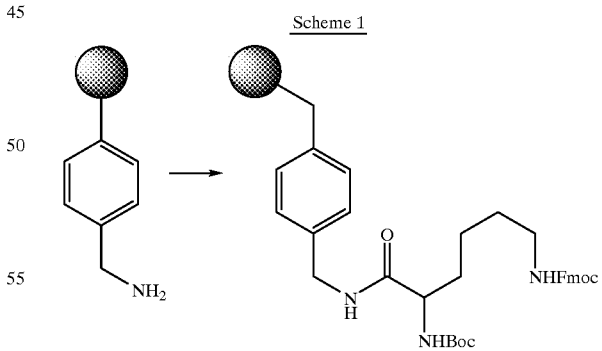

Selective removal of one protecting group from one site of the lysine-aminomethylpolystyrene produces a material which may be split into as many pools as desired. Each pool is differentially coded by the attachment of one or more fluorine codes in the form of, for example, fluorine containing carboxylic acids. An example of a bead tagged with Tag 3 is shown in Structure 1.

Structure 1

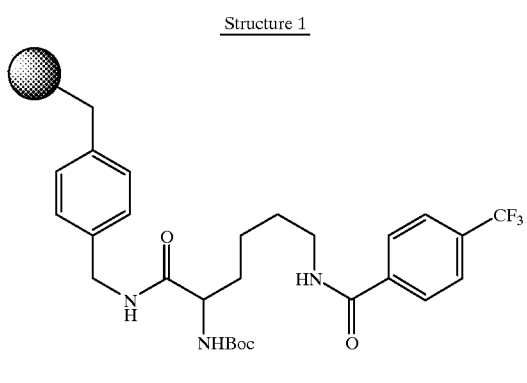

Each tagged pool is now ready for attaching a suitable combinatorial library linker (e.g., a Wang linker) to produce a coded resin suitable for constructing a combinatorial library. From Structure 1, one simply deprotects the remaining amine and attach an appropriate linker. Structure 2 illustrates one such coded resin.

Structure 2

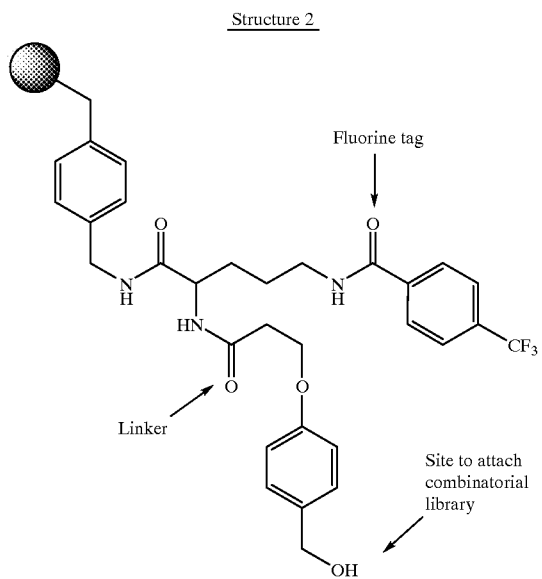

Schemes 2–8 illustrate direct incorporation of fluorine onto the polystyrene resin as an alternative tagging method. Scheme 2 illustrates an aryl halide coupling to a fluorine containing amine. Scheme 3 illustrates an aryl halide coupling to a fluorine containing acetylene. Scheme 4 illustrates an Friedel-Crafts coupling of the polystyrene aromatic moiety to the acid halide derivative of a fluorine containing carboxylic acid (exemplified by Tags 1–57). Scheme 5 illustrates the coupling of the polystyrene aromatic moiety to a fluorine containing aryl borane by the Suzuki Reaction. Scheme 6 illustrates a displacement reaction, wherein the nucleophile is the phenolic hydroxide, and the electrophile is a fluorine containing moiety having a leaving group. The ordinary artisan would understand that many other nucleophiles and electrophiles are available for displacement reactions (e.g., amine nucleophiles, carbanion nucleophiles, enols, enamines, acetylene anions etc. vs. carbonyl electrophiles, enones, etc.). Scheme 7 illustrates a coupling of amines and aldehydes by reductive amination: Scheme 8 illustrates a coupling of aromatic and alkyl hydroxides by the Mitsunobu Reaction. The ordinary artisan would understand that, in addition to the phenolic hydroxides, the acidic component can also include carboxylic acids, imides, oximes etc.

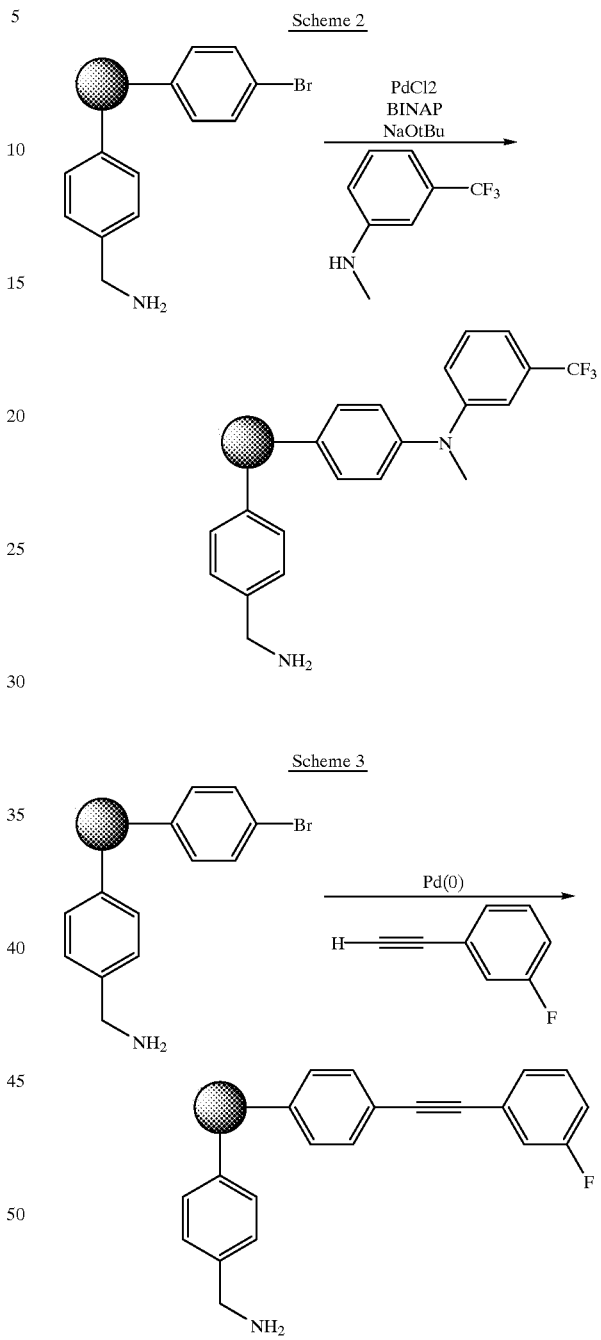

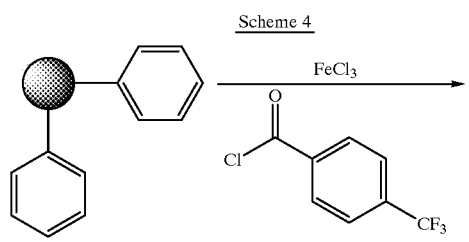

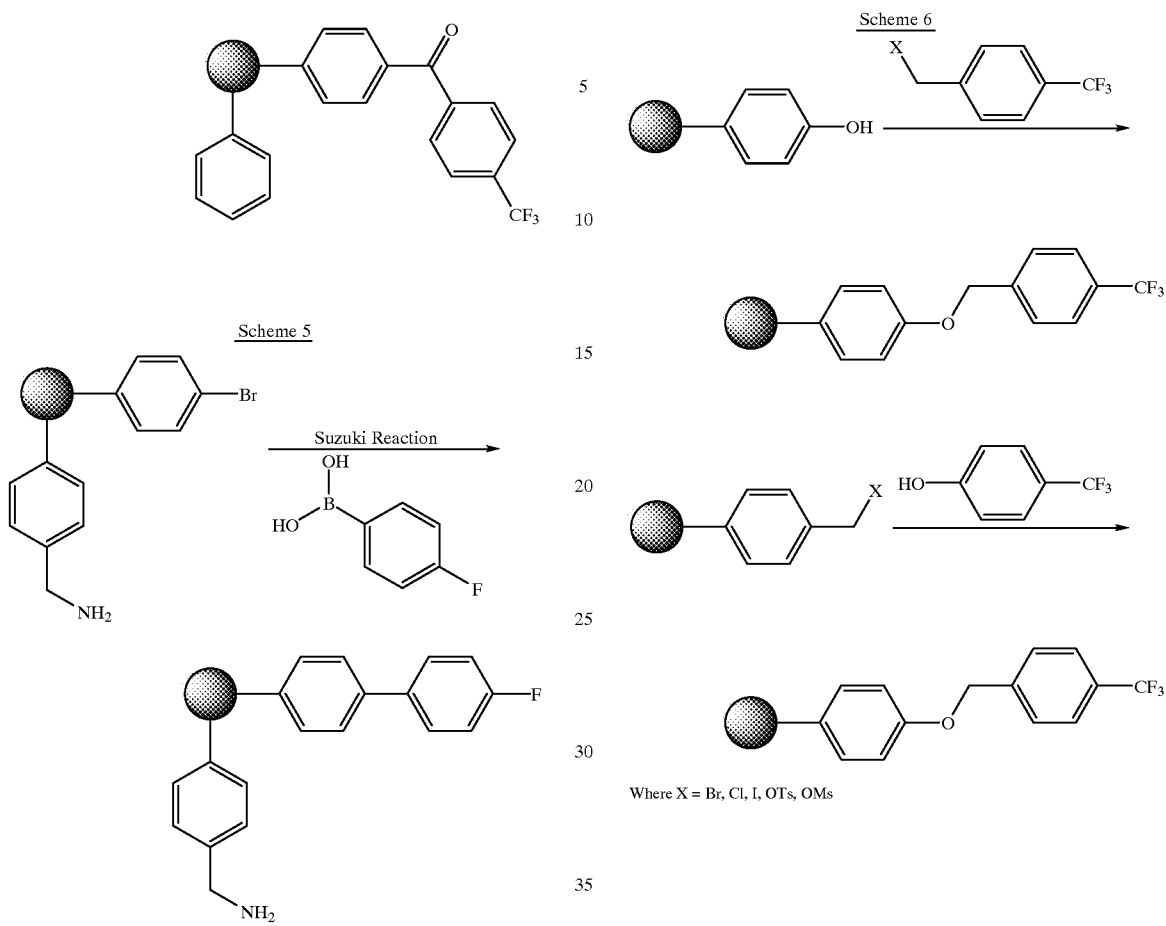
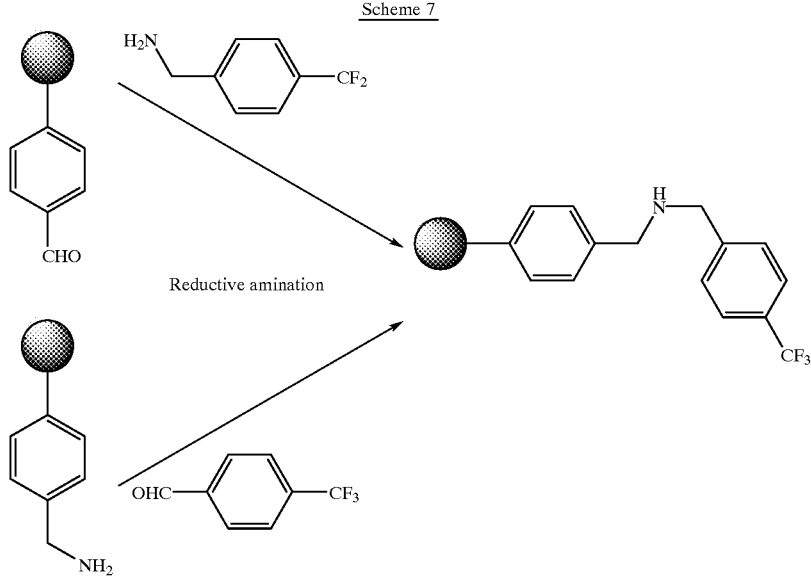

Scheme 8

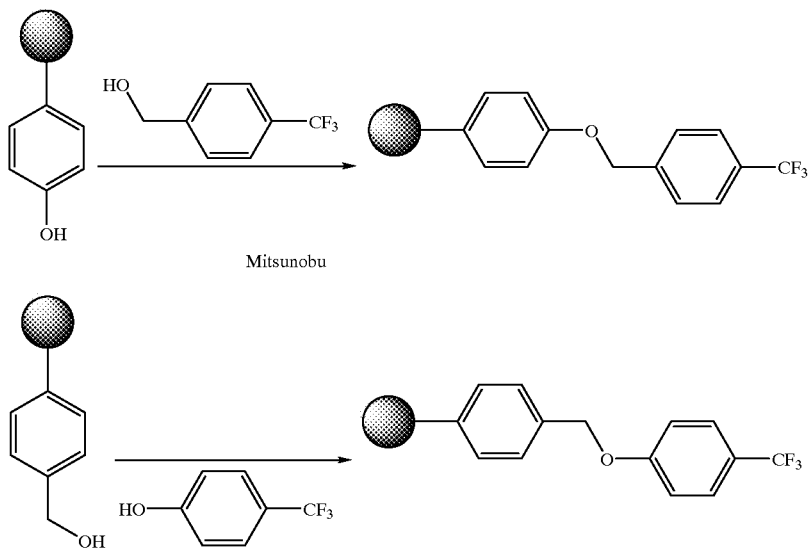

Other examples of methods of attaching tags to the solid support include, but are not limited to: carbene insertion on to an aromatic moiety; diaryl diazonium coupling; and Mannich reaction by a phenol or aniline moiety with formaldehyde and a secondary amine. One can also mask a potential tagging site by nitrating the aromatic group of a solid support that comprises aromatic moieties. At the desired point in during library construction, one could reduce the nitro moiety to the amine with tin chloride. The amine becomes a taggable site. The ordinary artisan would understand that numerous methods of attaching tags to solid supports are appropriate for the numerous different solid supports and numerous different fluorine containing tags that are available.

Coding the Combinatorial Libraries

The ordinary artisan understands that numerous permutations for coding and attaching combinatorial library exist. For example, one can attach a linker and a library core first before coding the bead. Scheme 9 illustrates three examples of tagging the bead after construction of the combinatorial library has begun.

Scheme 9

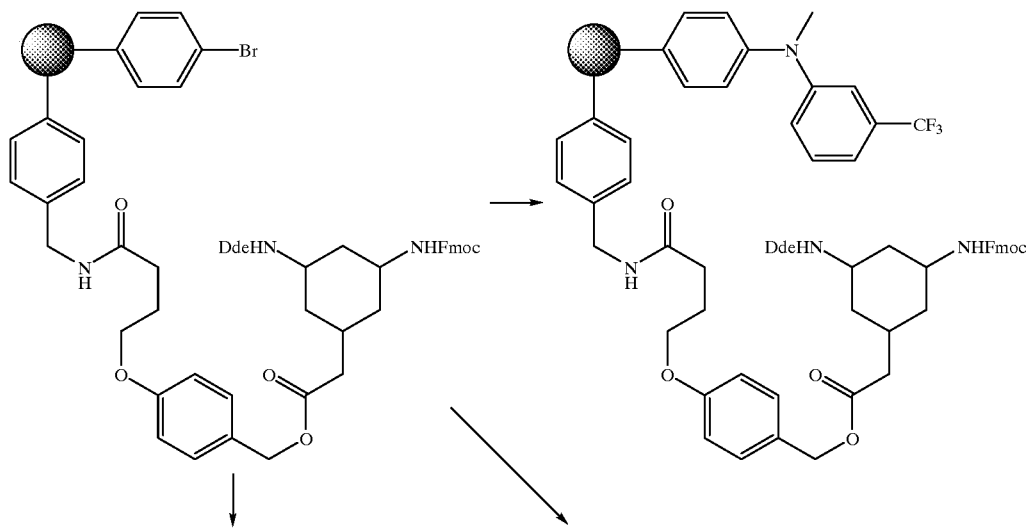

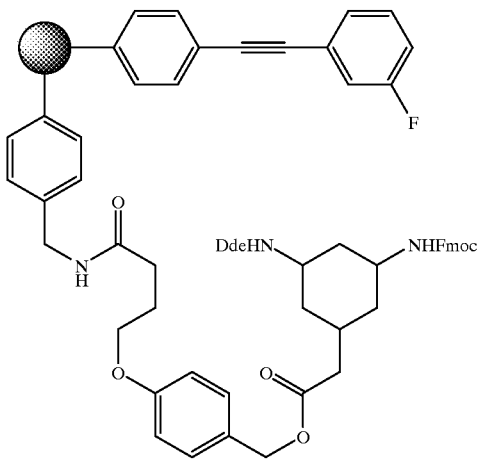

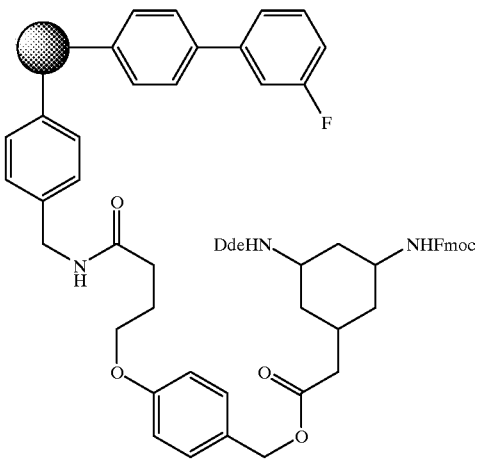

From Scheme 9, one obtains a bead that has a combinatorial linker attached to a combinatorial library core, and an orthogonally attached tag (or code). A core is any moiety that has more than one site for attaching additional units. As shown in Scheme 9, a core need not be a traditional amino acid. In fact, it need not be an amino acid at all. From Scheme 9, one can selectively deprotect one of the functionalities on the core, and attach a different monomers on to each of the three tagged combinatorial construct to build a diversity library, as shown in Structures 3–5.

Structure 3

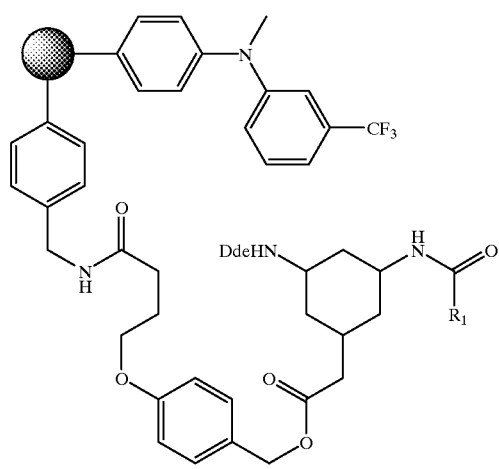

Structure 4

Structure 5

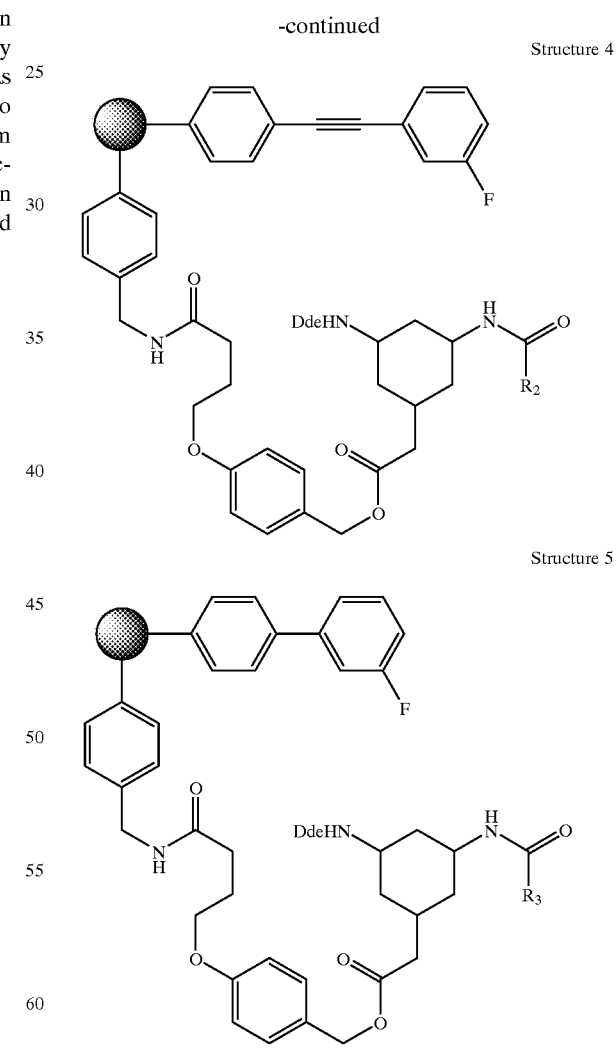

One can now mix Structures 3–5 together, deprotect at the second functionality on the core, and react all three with a second monomer. To create even greater diversity, one can split the mixture into pools to react with several different set of second monomers. For example, a pool containing Structures 3, 4 and 5 could be deprotected at the second amine, and reacted with $R_4$—X to complete construction of the combinatorial library. Another pool could be deprotected and reacted with $R_5$—(CO)—X. Structures 6–8 illustrates the pool reacted with $R_4$—X. Although the pool now contains a mixture of Structures 6–8, one can chose any bead from the mixture, and determine which member of the combinatorial library is on that particular bead by FNMR.

Structure 6

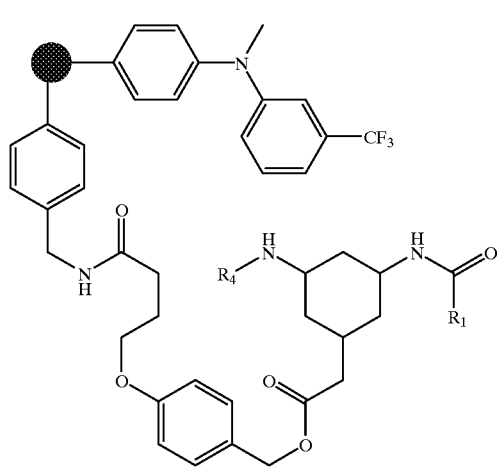

Structure 7

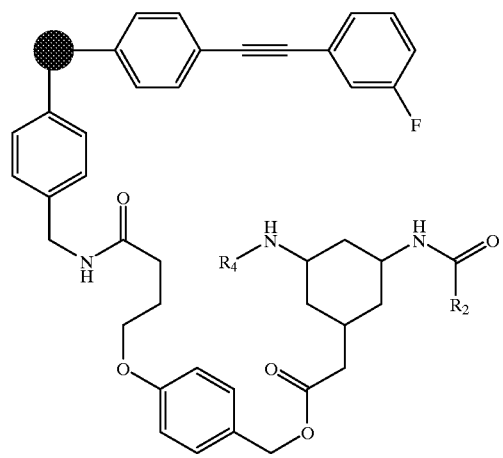

Structure 8

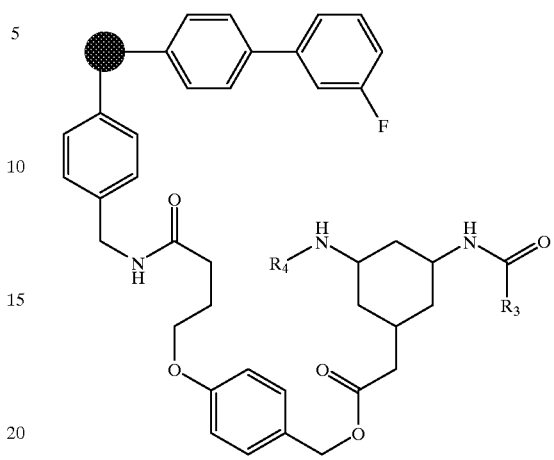

In another preferred embodiment, each chemical step is coded by covalently attaching an orthogonally protected, and tagged Lys, Orn or Dap to the bead. As each step of the library synthesis proceeds, one protecting group of the Lys, Orn or Dap is removed and attached to another tag or another protected Lys, Orn or Dap with another distinctive tag. Multiple reactions can be tagged in this manner. Scheme 10 illustrates the attachment of a lysine, pre-tagged with a Tag 1, to a bead containing a lysine linker.

Scheme 10

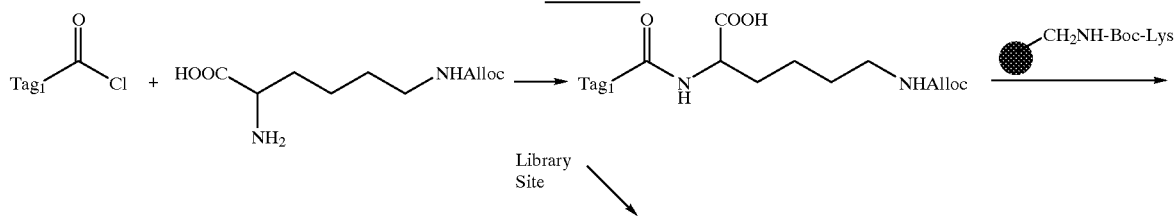

Library Site

-continued

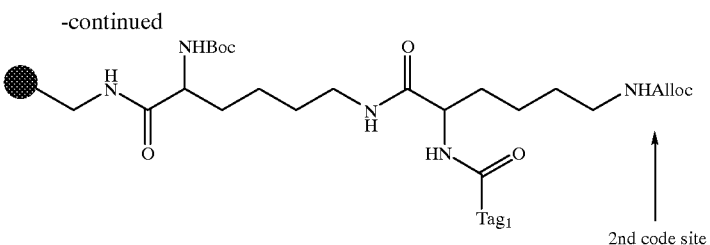

2nd code site

One can now deprotect the Boc protected amine or the Alloc protected amine. Either of the remaining protected amines can act as the library site or the code site, although the Boc protected amine is indicated as the library site in Scheme 10. One can now begin construction of a library by attaching a first monomer, followed by a second tag to code the attachment of a second monomer. Scheme 11 shows that the product of Scheme 10 with a first unit (amino acid A) attached by linker L can be coded with a second Tag 2, and reacted with a second unit (amino acid B) to produce a unique FNMR signature which represents the AB dipeptide.

Scheme 11

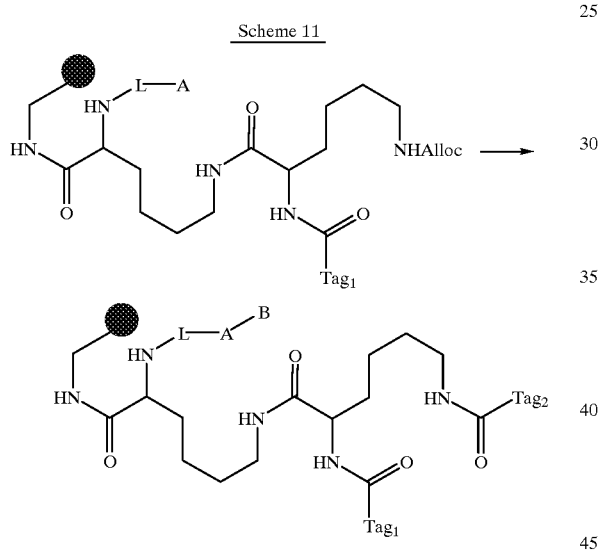

The protecting group can be a Dde, Fmoc, Bpoc, Alloc, or another common protecting group whose cleavage is compatible with, and orthogonal to the linker and library. The FNMR signature of the bead can be read either before or after cleavage and, based on the signals observed, the reaction history of the bead can be ascertained.

Structure 9 illustrates a core where the functional groups on all of the orthogonal attachment sites are different. As an example, a bead having a free hydroxyl moiety can be attached via the acid moiety. Then, the a monomer is attached to the amine, followed by a second monomer at the aldehyde moiety. Structures 10 and 11 exemplify the first unit, while Structures 12 and 13 exemplify the second unit. The ordinary artisan would recognize that the moiety attached and the order of attachment can vary, and that protection and deprotection of the functional groups may be necessary. As a further example, if one attaches a bead by the amine moiety on the core, then diversification could take place on the acid moiety.

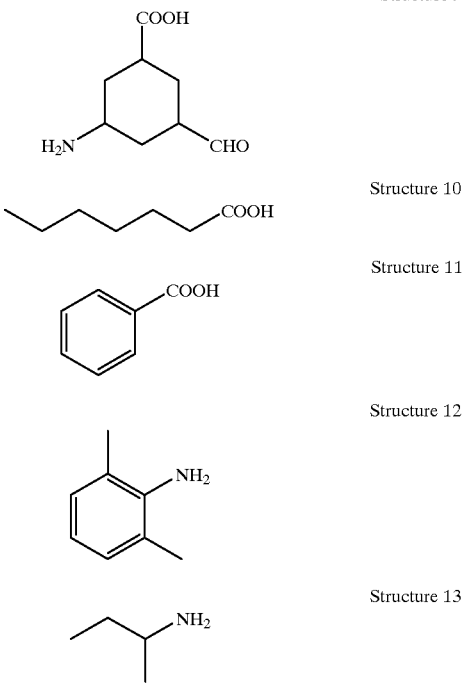

Structure 9

Structure 10

Structure 11

Structure 12

Structure 13

Structures 14 and 15 illustrates attachment of the core to each of two tagged beads via a generic linker, L. In addition, they show the attachment of Structure 10 to the beads coded with Tag 1 and the attachment of Structure 11 to the beads code with Tag 2.

Structure 14

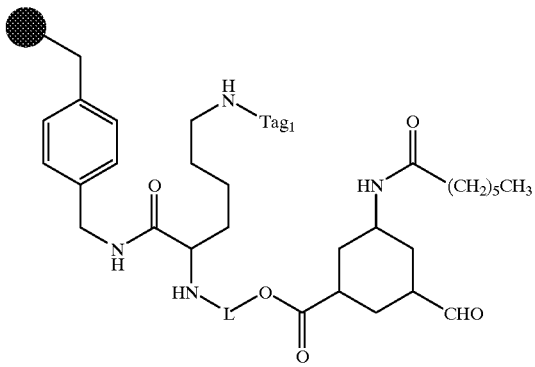

Structure 15

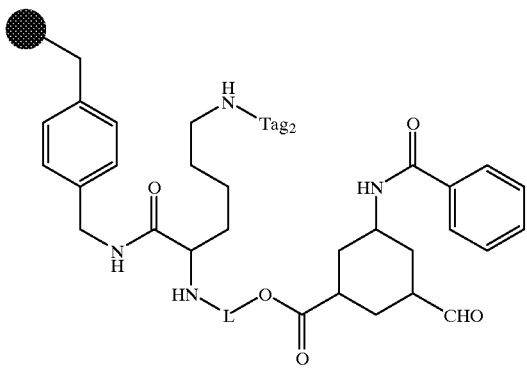

Structures 14 and 15 are then mixed together, and then split apart into two pools (Pools 1 and 2) of beads that are mixtures of Structures 14 and 15. Attachment of Structure 12 to Pool 1 results in a mixture of Structures 16 and 17.

Structure 16

Structure 17

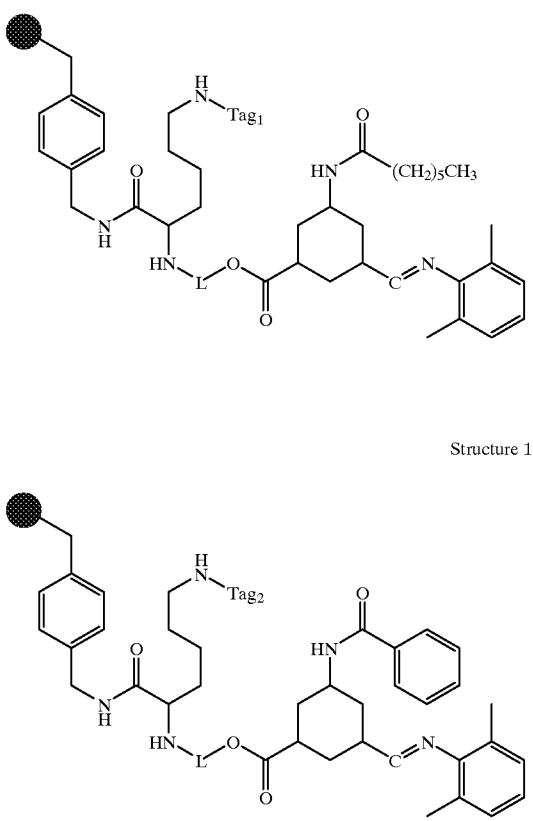

From Pool 1, one can determine which member of the library is attached to any bead by simply reading the FNMR tag. Tag 1 would indicate the member corresponding to Structure 16, while Tag 2 would indicate the member corresponding to Structure 17. Similarly, attachment of Structure 13 to Pool 2, would result in a mixture of Structures 18 and 19. Once again, one determines the structure on each bead by reading Tags 1 or 2 by FNMR.

Structure 18

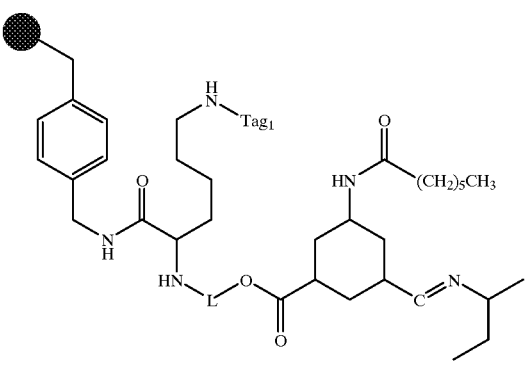

Structure 19

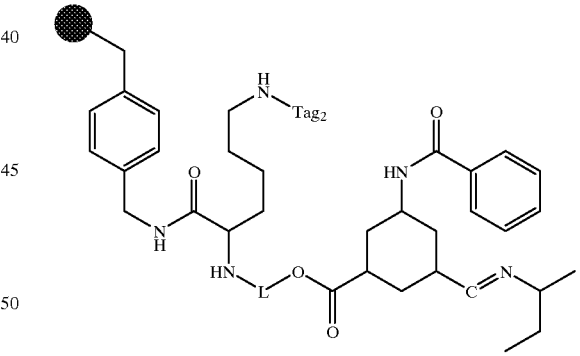

Structure 20 illustrates the use of a lysine code linker to attach two tags to code the attachment of two monomer units to the library core.

Structure 20

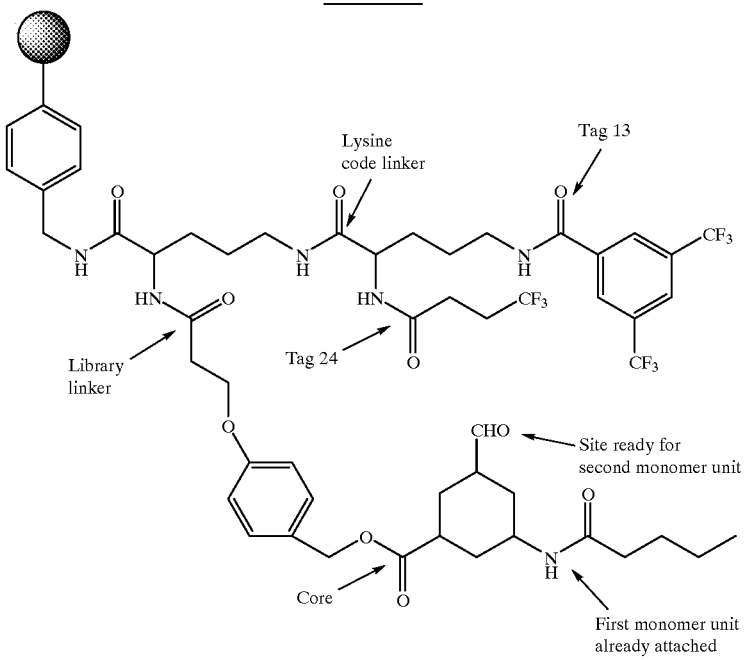

Scheme 12 illustrates another preferred embodiment where two different lysine linkers are used for orthogonal attachment of different Tags.

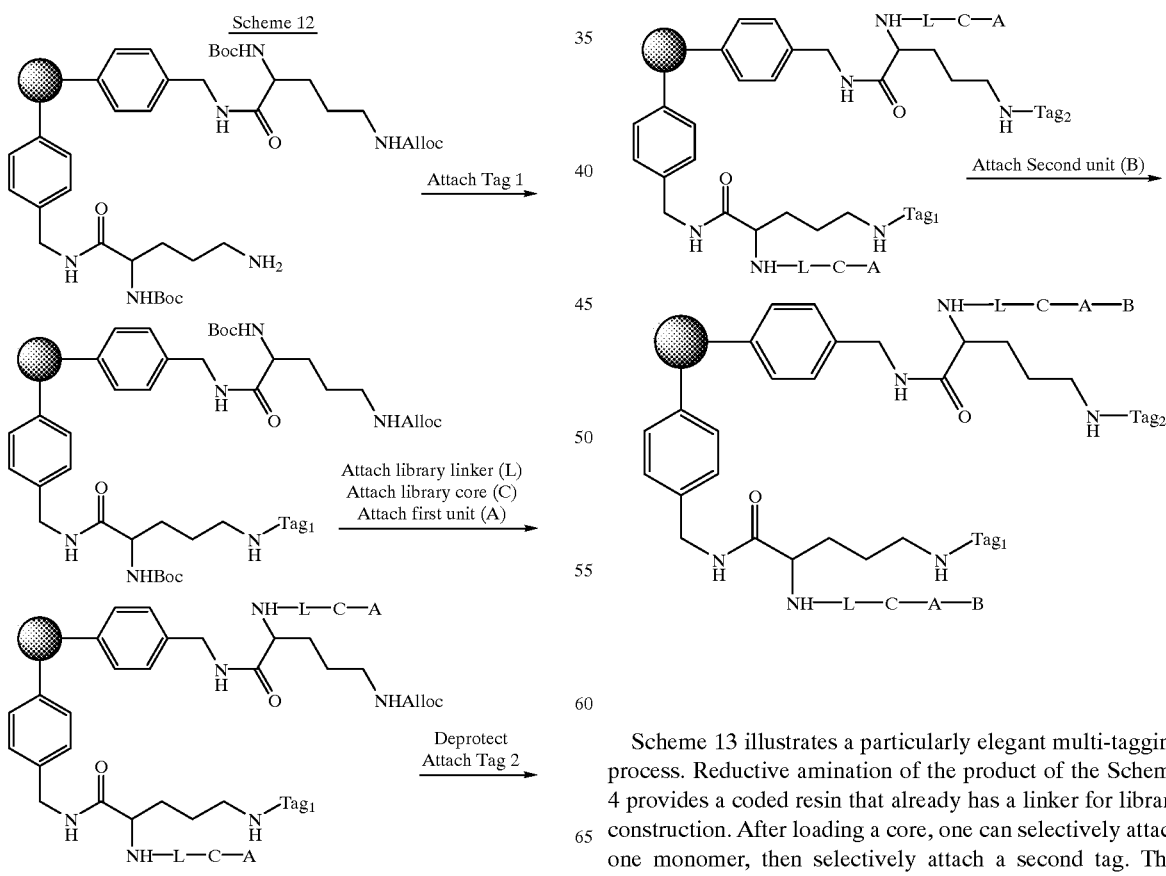

Scheme 13 illustrates a particularly elegant multi-tagging process. Reductive amination of the product of the Scheme 4 provides a coded resin that already has a linker for library construction. After loading a core, one can selectively attach one monomer, then selectively attach a second tag. This product is now ready for second monomer attachment.

Scheme 13
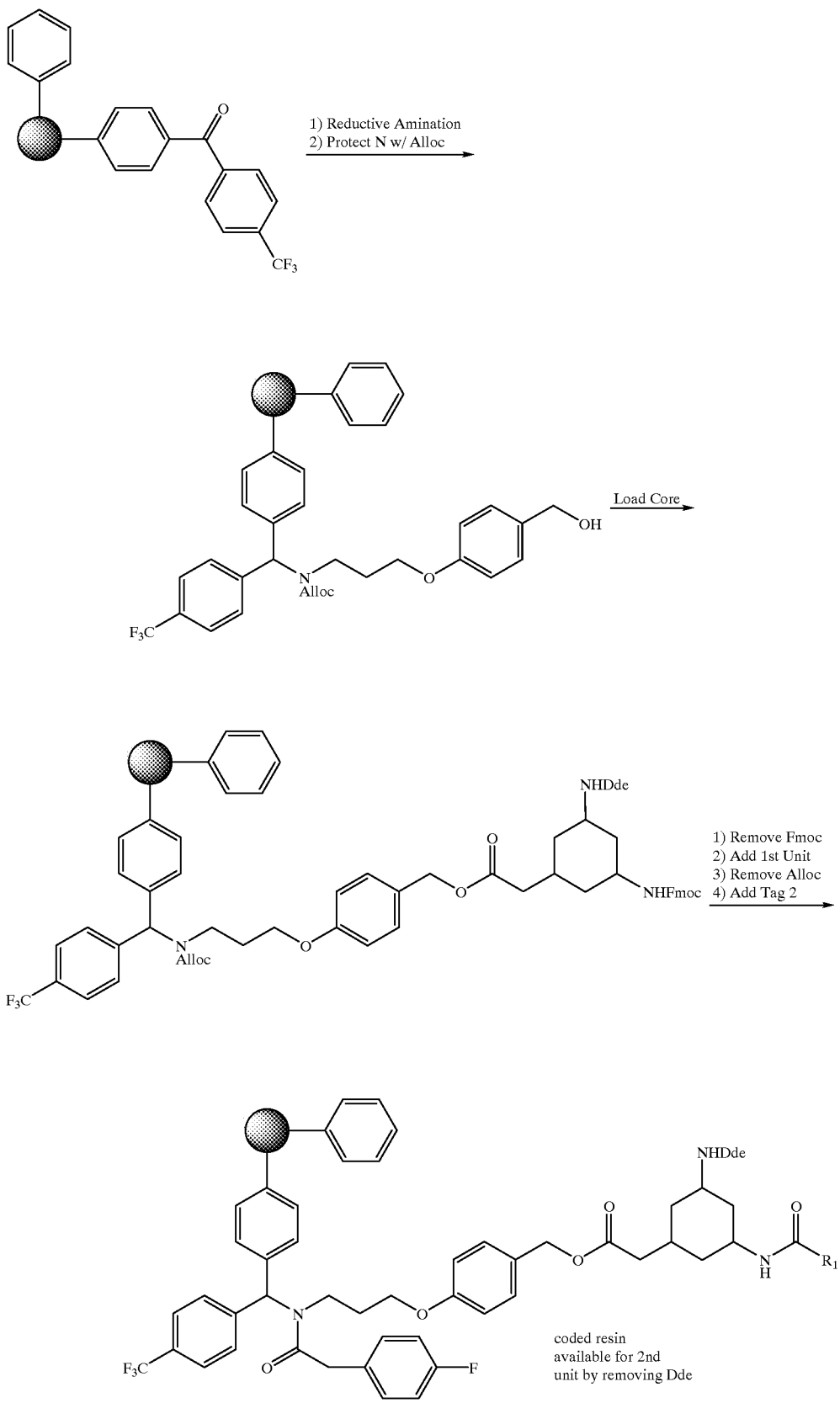

Scheme 14 illustrates another method of modifying the product of Scheme 4 for library construction.

Scheme 14

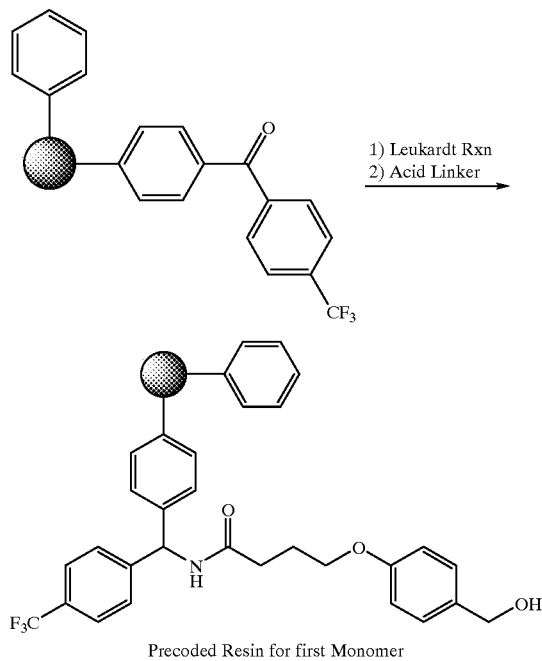

1) Leukardt Rxn
2) Acid Linker

Precoded Resin for first Monomer

Library Linkers

Numerous functionalities and reactants can be used to facilitate selective or partial detachment of the library from the bead. Convenient examples of such linkers include ethers such as substituted benzyl ether or derivatives thereof (e.g., benzylhydryl ether, indanyl ether, etc.) that can be cleaved by acidic or mild reductive conditions. Alternatively, one can employ P-elimination, where a mild base can serve to release the product.

One can also use acetals, including the thio analogs thereof, where detachment is accomplished by mild acid, particularly in the presence of a capturing carbonyl compound. These can be formed by combining formaldehyde, HCl and an alcohol moiety to form an α-chloroether. Then, this is coupled with a hydroxy functionality on the bead to form the acetal.

Various photolabile linkages (e.g., O-nitrobenzoyl, 7-nitroindanyl, 2-nitrobenzhydryl ethers or esters, etc.) can also be employed. Esters and amides can also serve as linkers, where half-acid esters or amides are formed, particularly with cyclic anhydrides, followed by reaction with hydroxyl or amino functionalities on the bead, using a coupling agent such as DCC. Moreover, peptides are also potential linkers, where the sequence is subject to enzymatic hydrolysis, particularly where the enzyme recognizes a specific sequence. Carbonates and carbamates can be prepared using carbonic acid derivatives, e.g., phosgene, carbonyl diimidazole, etc. and mild base. The linker can be cleaved using acid, base or a strong reducing agent.

Where a linker is used, functionalities on the solid support can be modified through a non-labile linkage such as an ester bond, amide bond, amine bond, ether bond, or through a sulfur, silicon, or carbon atom, depending upon whether one wishes to remove the product from the bead or resin. Conveniently, the bond to the bead or resin is permanent. Alternately, the bond between the linker and bead or resin can be labile or cleavable. Depending upon the nature of the linking group bound to the particle, reactive functionalities on the bead may not be necessary where the manner of linking allows for insertion into single or double bonds, such as is available with carbenes and nitrenes or other highly-reactive species. In this case, the cleavable linkage can be provided in the linking group which joins the product to the bead.

Preferred linker are Lys, Orn, or Dap linkers protected with a photocleavable protecting group at the epsilon, gamma or delta amino group. Limited irradiation produces partial cleavage of this photocleavable group, therefore liberating a site for the incorporation of one or more tags. An example of a library linker is a protected 4-hydroxymethyl phenoxyacetic acid (Wang linker) bearing a protective group to mask the alcohol functionality.

The following examples illustrate the preferred embodiment of the present invention, without limiting the claims or the specification. The ordinary artisan will readily appreciate that changes and modifications to the specified embodiments can be made without departing from the scope and spirit of the invention.

EXAMPLES

Example 1
Making Tagged Resin by Amide Coupling Loading Diprotected Lysine onto the Aminomethylpolystyrene Bead (Scheme 1)

About 2.25 g (4.8 mmol) of N-α-BOC-N-ε-FMOC lysine, about 1.69 ml. (9.6 mmol) of N,N-diisopropylethylamine and about 2.24 g (4.8 mmol) of PyBroP was added successively to a suspension of about 2.00 g (2.4 mmol capacity) of aminomethylpolystyrene resin in about 30 ml. of DCM. The suspension was rotated at room temperature for about 1.5 hr, and drained. The same amounts of reagents were added again to the resin, and the resulting suspension was rotated at room temperature for about 1.5 hr. The suspension was drained and the resin was washed successively with five portions of about 30-ml. DMF and five portions of about 30-ml. DCM, and dried in vacuo.

FMOC Deprotection

About 30 ml. of 20% piperidine in DMF was added to about 2 g. of the above prepared N-α-BOC-N-ε-FMOC lysine aminomethylpolystyrene. The suspension was rotated at room temperature for about 15 minutes, after which the solvent was drained. About 30 ml. of an additional 20% piperidine in DMF was added and the suspension rotated at room temperature for about 15 minutes, after which the solvent was drained. Then the resin was washed sequentially with portions of about 30 ml. of DMF, $H_2O$, DMF, DCM, $H_2O$, EtOH and MeOH.

Attaching Fluorine Tags
Pool 1 (Tag 1)

About 2 ml of DMF was added to a 100 mg pool of the above prepared N-α-Boc-lysine aminomethylpolystyrene. The mixture was allowed to sit for about 30 minutes to allow the polystyrene to swell. Thereafter, 3-(4-fluorophenyl) propionic acid (40 mg, 0.24 mM, 2 eq.) was added to the mixture, followed by 1,3-diisopropylcarbodiimide (56 ml, 0.36 mM, 3 eq.) and 1-hydroxybenzotriazole hydrate (16 mg, 0.12 ml, 1 eq.). This mixture was rotated for 16 hours at room temperature. Then, the resin was transferred to a fritted funnel and washed sequentially with DMF, distilled water, ethanol, dichloromethane and methanol (about 20 ml aliquots of each solvent, allowing 15 minutes equilibration before removing each solvent). A single bead FNMR spectrum from this pool contained a single peak at −118 ppm (See FIG. 1). Note that minor variations, well-known to the ordinary artisan, may occur in the chemical shift of the fluorine peaks (Tag 1 listed as −117 ppm, but shown as −117.71 ppm). However, these minor variations do not substantially change the effectiveness of fluorine tagging as a method of library member identification.

Pools 2–4 (Tags 2–4)

Figure 2:
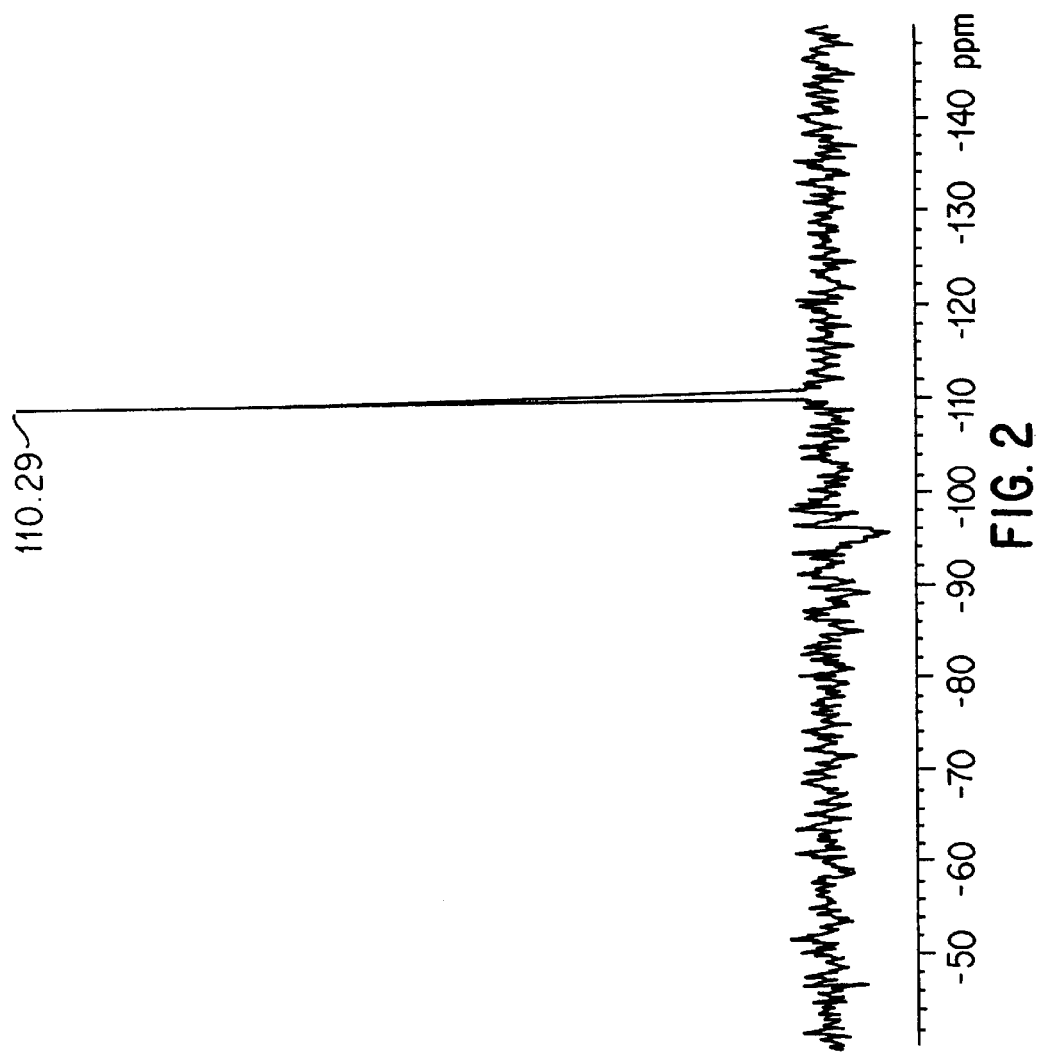

The method used to prepare Pool 1 was used to attach 3,5-difluorophenylacetic acid (Tag 2, 41 mg, 0.24 mM, 2 eq.). A single bead FNMR spectrum from Pool 2 contained a single peak at −110 ppm (See FIG. 2).

The method used to prepare Pool 1 was used to attach 4-trifuloromethylbenzoic acid (Tag 3, 46 mg, 0.24 mM, 2 eq.). A single bead FNMR spectrum from Pool 3 contained a single peak at −63 ppm.

The method used to prepare Pool 1 was used to attach 4-(trifluoromethoxy)benzoic acid (Tag 4, 49 mg, 0.24 mM, 2 eq.). A single bead FNMR spectrum from Pool 4 contained a single peak at −58 ppm.

Pool 5 (1:1 Tags 1/2)

About 2 ml of DMF was added to a 100 mg pool of the above prepared N-α-Boc-lysine aminomethylpolystyrene. The mixture was allowed to sit for about 30 minutes to allow the polystyrene to swell. Thereafter, a solution of premixed 3-(4-flourophenyl)-propionic acid (20 mg, 0.12 mM) and 3,5-difluorophenylacetic acid (21 mg, 0.12 mM) in DMF was added to the mixture, followed by 1,3-diisopropylcarbodiimide (56 ml, 0.36 mM, 3 eq.) and 1-hydroxybenzotriazole hydrate (16 mg, 0.12 mM, 1 eq.). This mixture was rotated for 16 hours at room temperature. Then, the resin was transferred to a fritted funnel and washed sequentially with DMF, distilled water, ethanol, dichloromethane and methanol (about 20 ml aliquots of each solvent, allowing 15 minutes equilibration before removing each solvent). A single bead FNMR spectrum from this pool contained two fluorine peaks at −117 ppm and −110 ppm. The chemical shifts and the ratio of peak areas were reproducible from bead to bead.

Pools 6 (2:1 Tags 1/2) and 7 (1:2 Tags 1/2)

The method used to prepare Pool 5 was used to attach a mixture of 3-(4-flourophenyl)propionic acid (30 mg, 0.16 mM) and 3,5-difluorophenylacetic acid (10 mg, 0.08 mM). The single bead FNMR spectrum of Pool 6 contained two fluorine peaks at −117 ppm and −110 ppm. The chemical shifts and the ratio of peak areas were reproducible from bead to bead, with a distinct ratio than beads from Pool 5.

Figure 3:
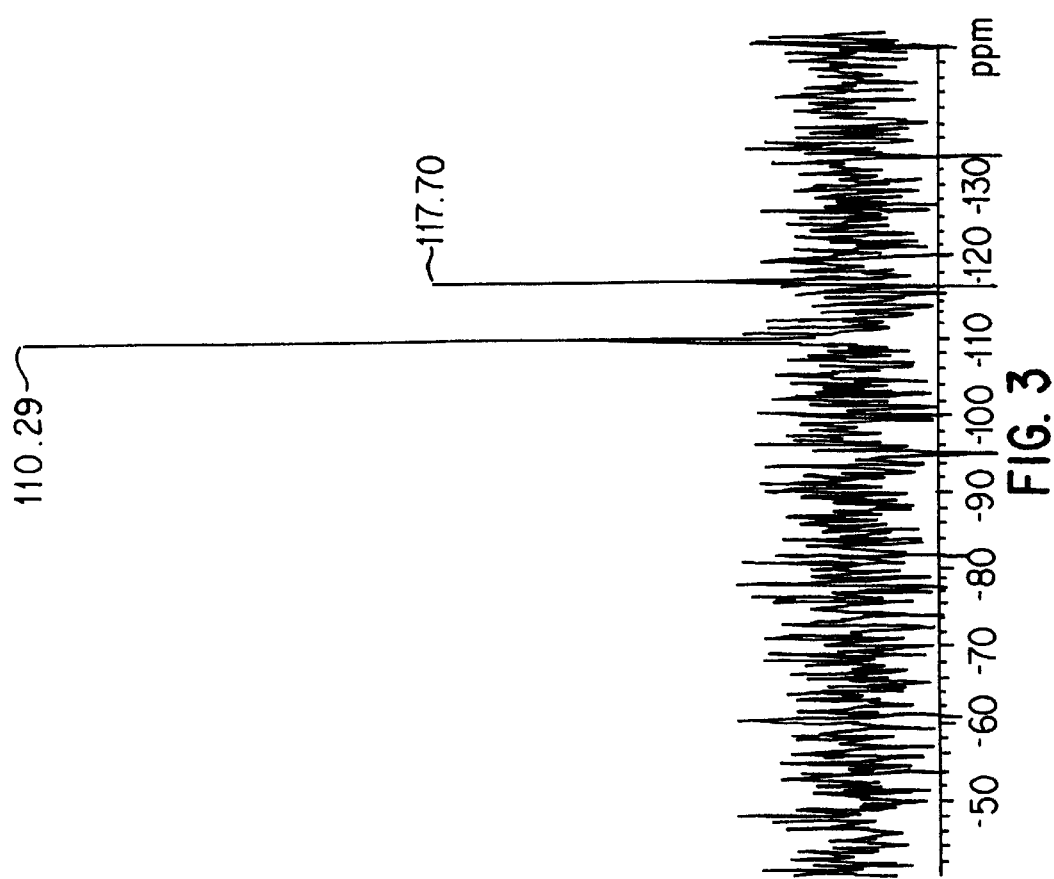
Figure 4:
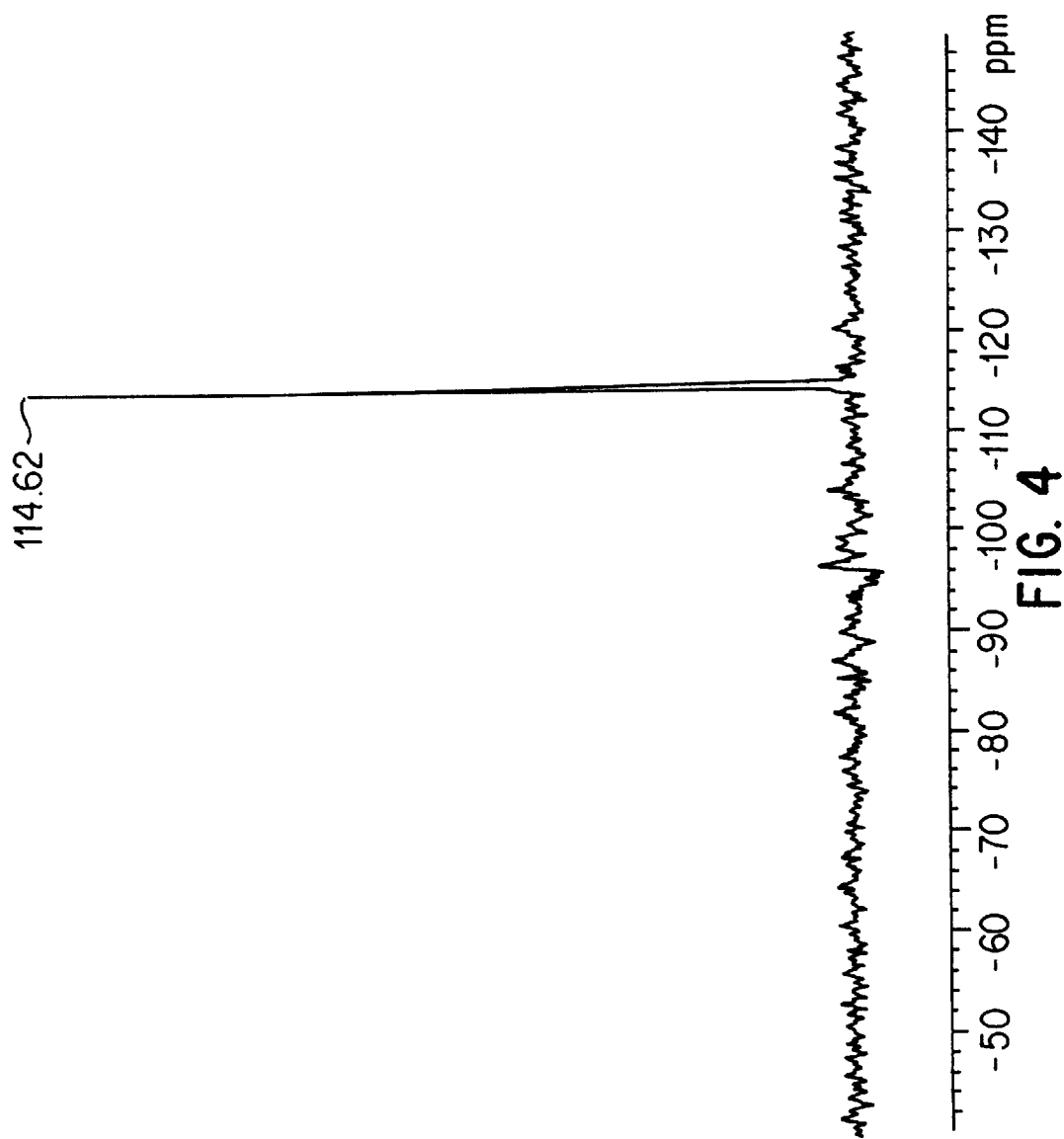
Figure 5:
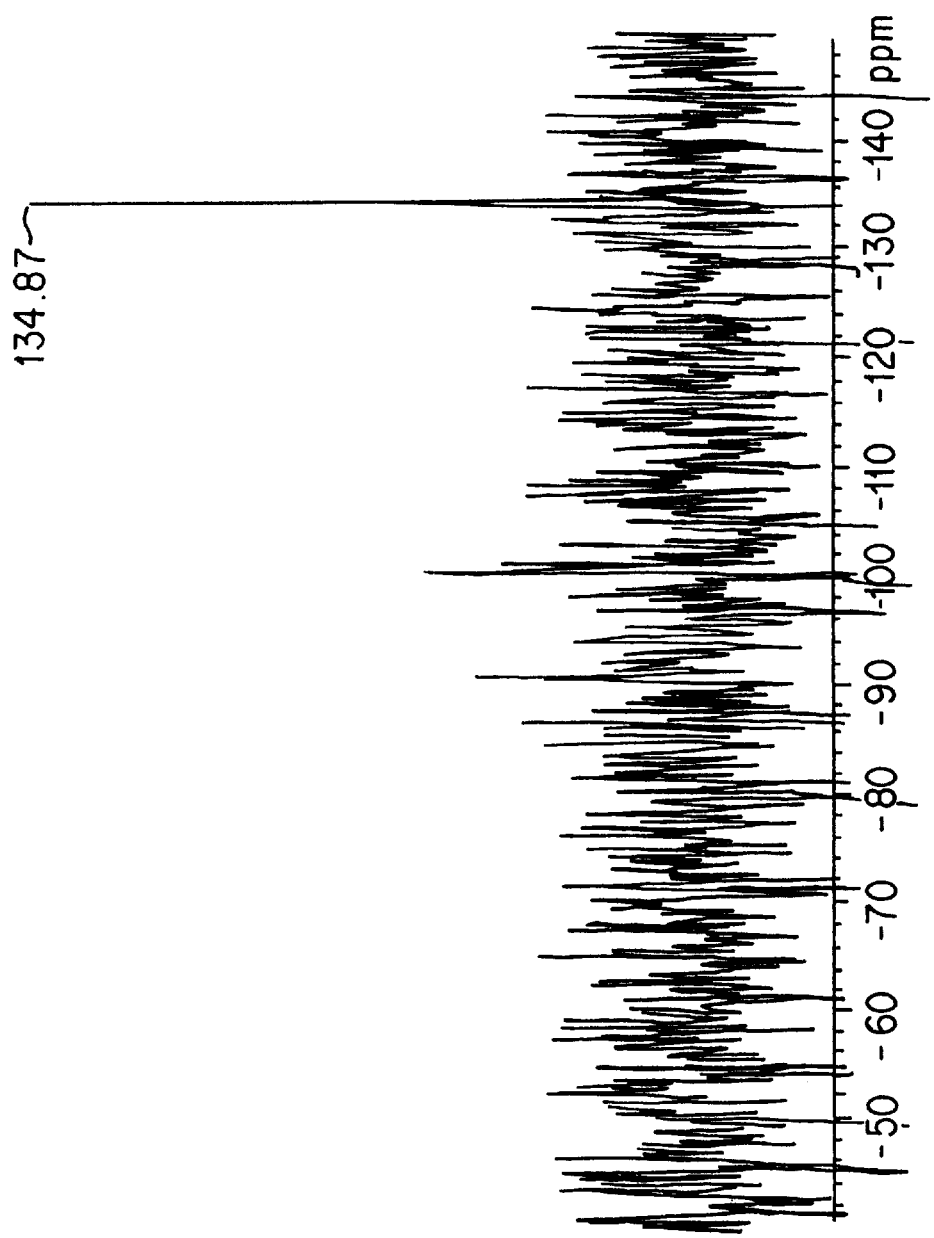
Figure 6:
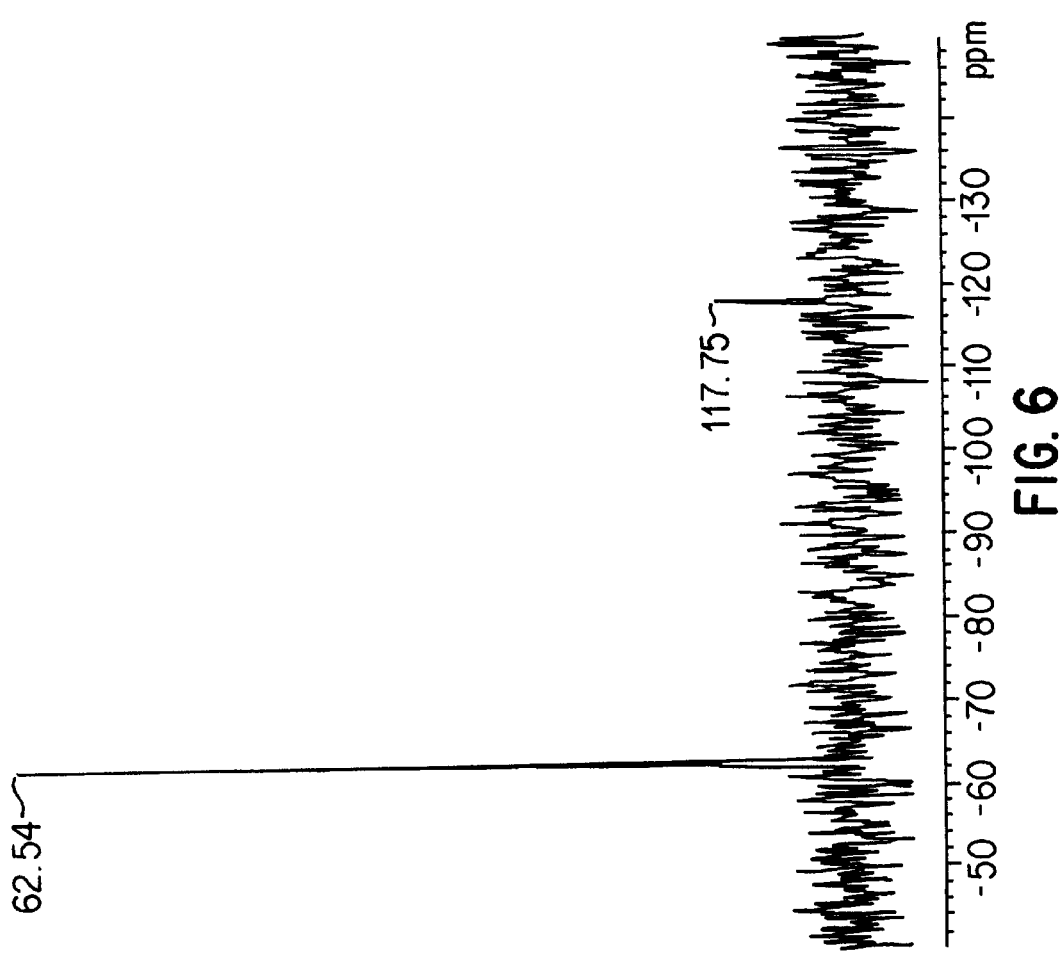
Figure 7:
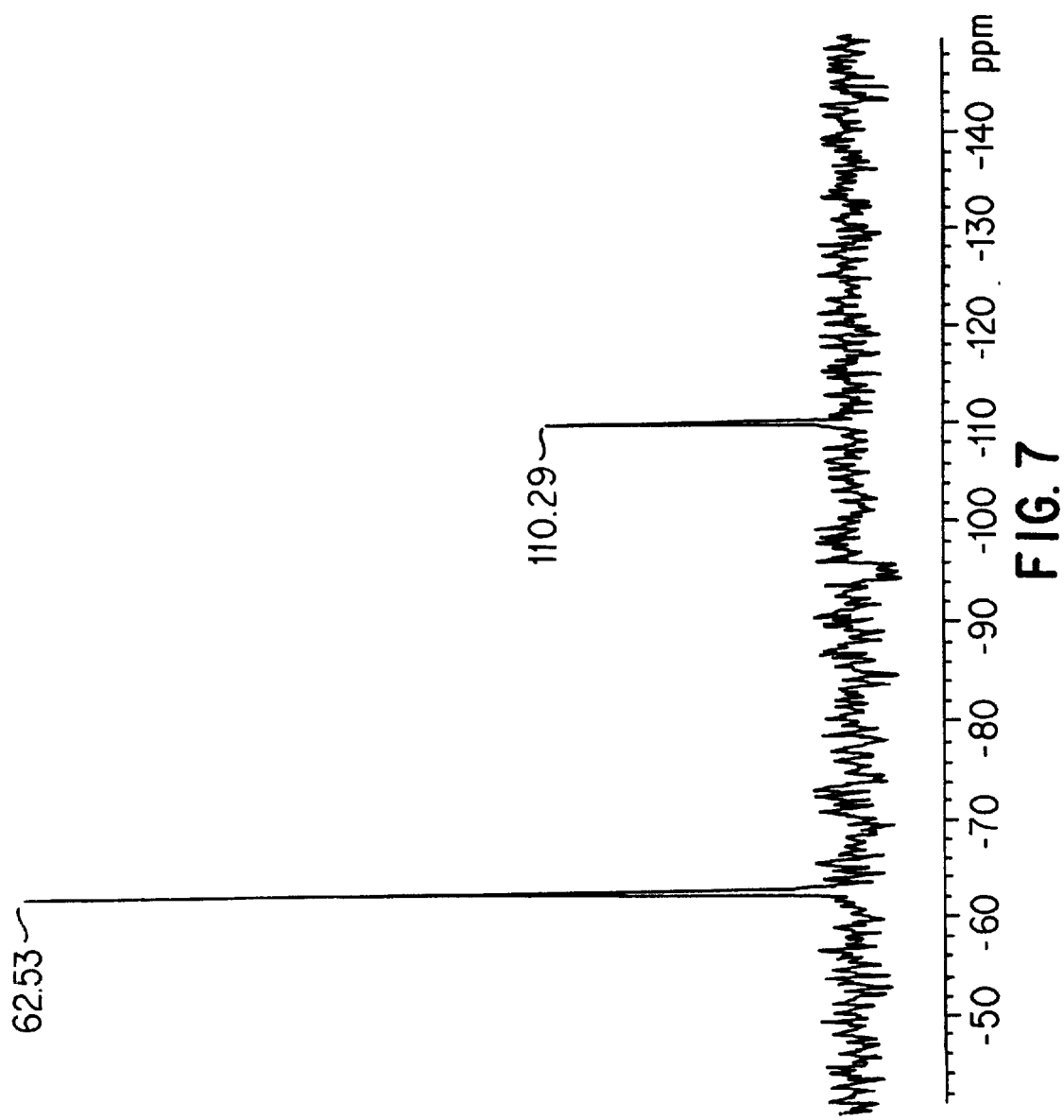
Figure 8:
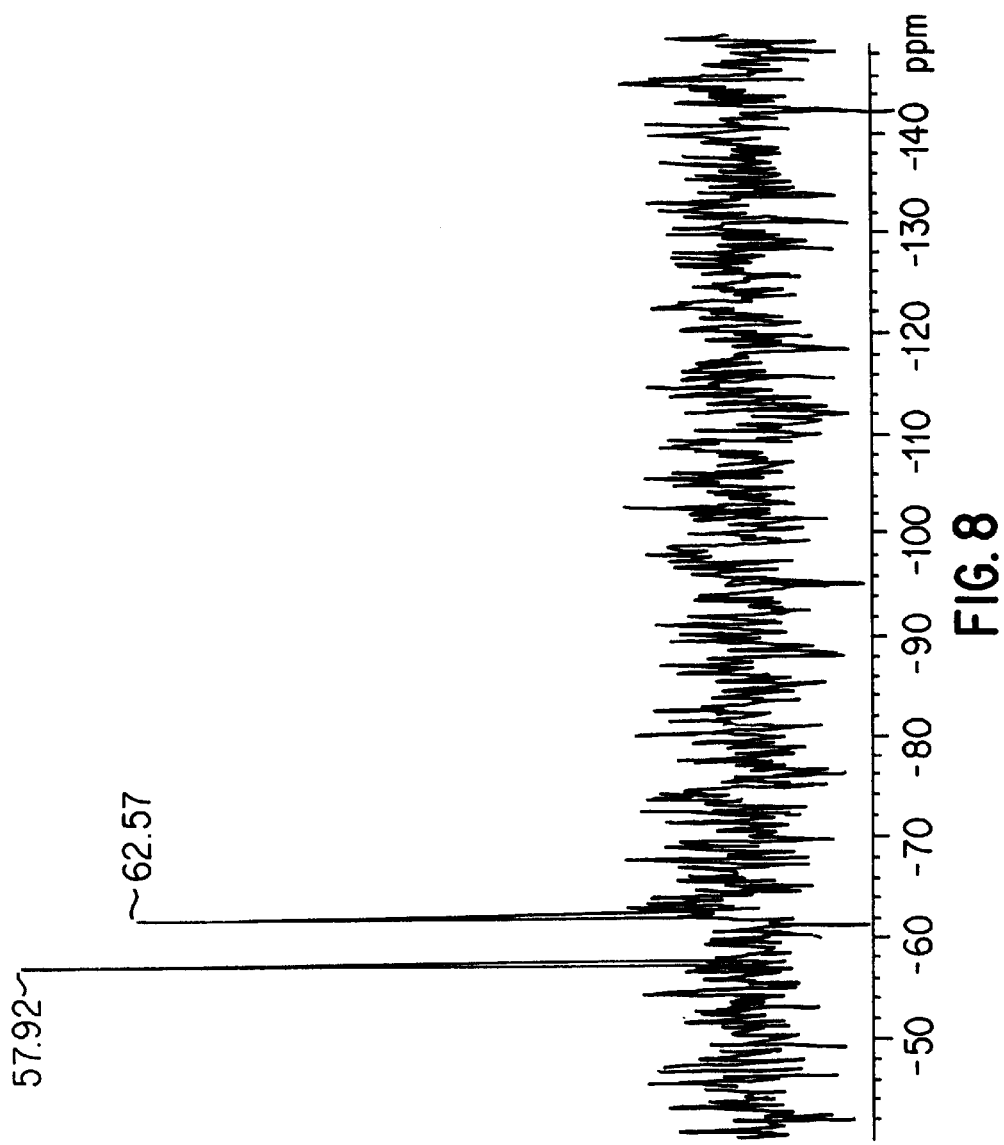
Figure 9:
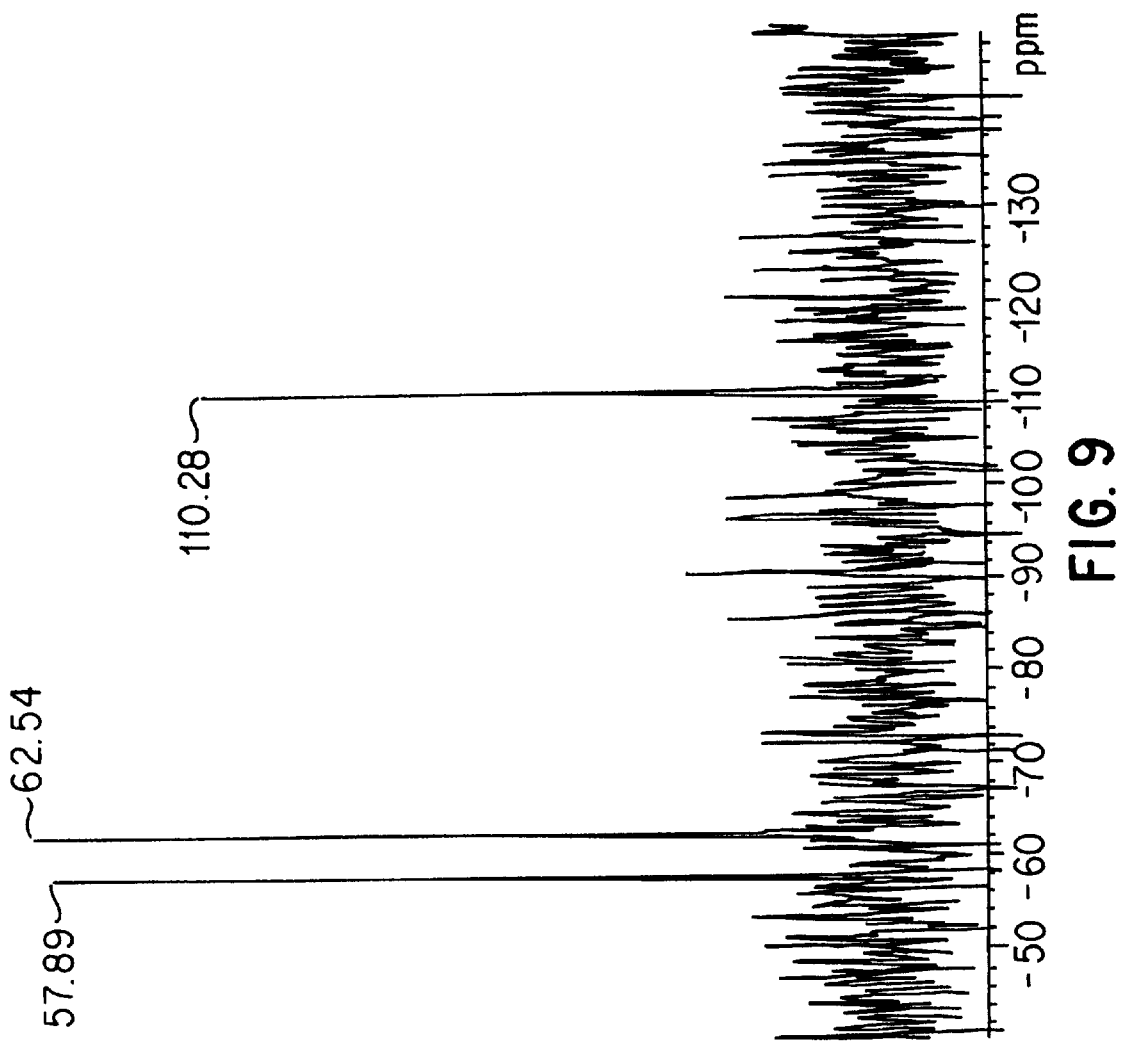

The method used to prepare Pool 5 was used to attach a mixture of 3-(4-flourophenyl)propionic acid (10 mg, 0.08 mM) and 3,5-difluorophenylacetic acid (31 mg, 0.16 mM). The single bead FNMR spectrum of Pool 7 contained two fluorine peaks at −117 ppm and −110 ppm (See FIG. 3). The chemical shifts and the ratio of peak areas were reproducible from bead to bead, with a distinct ratio than beads from Pools 5 and 6. Note that Tag 2, in addition to being twice as abundant as Tag 1, has also twice the number of fluorines as Tag 1. Accordingly, FIG. 3 shows about four times the peak area for Tag 2 compared with Tag 1.

Additional Pools

Figure 10:
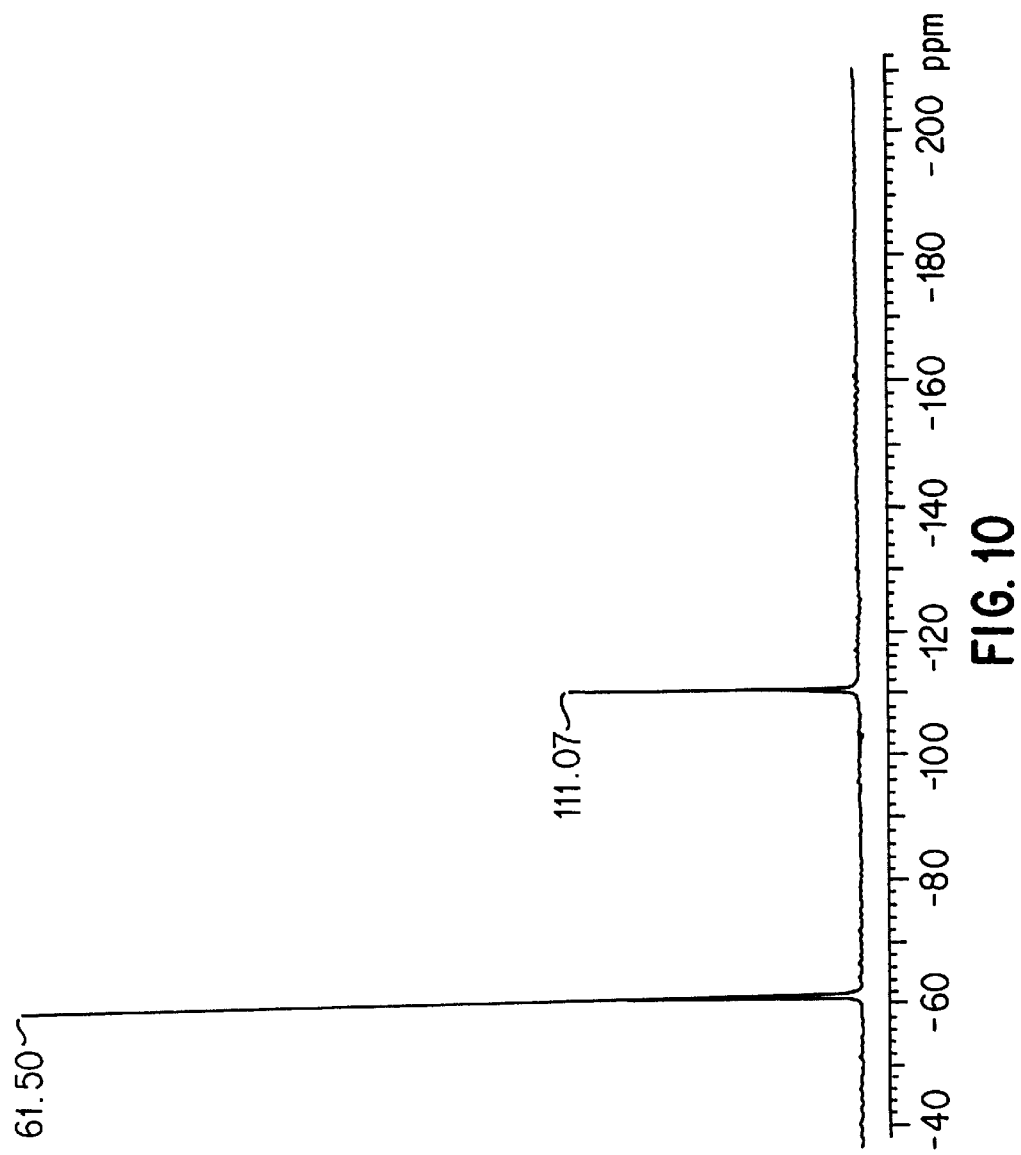
Figure 11:
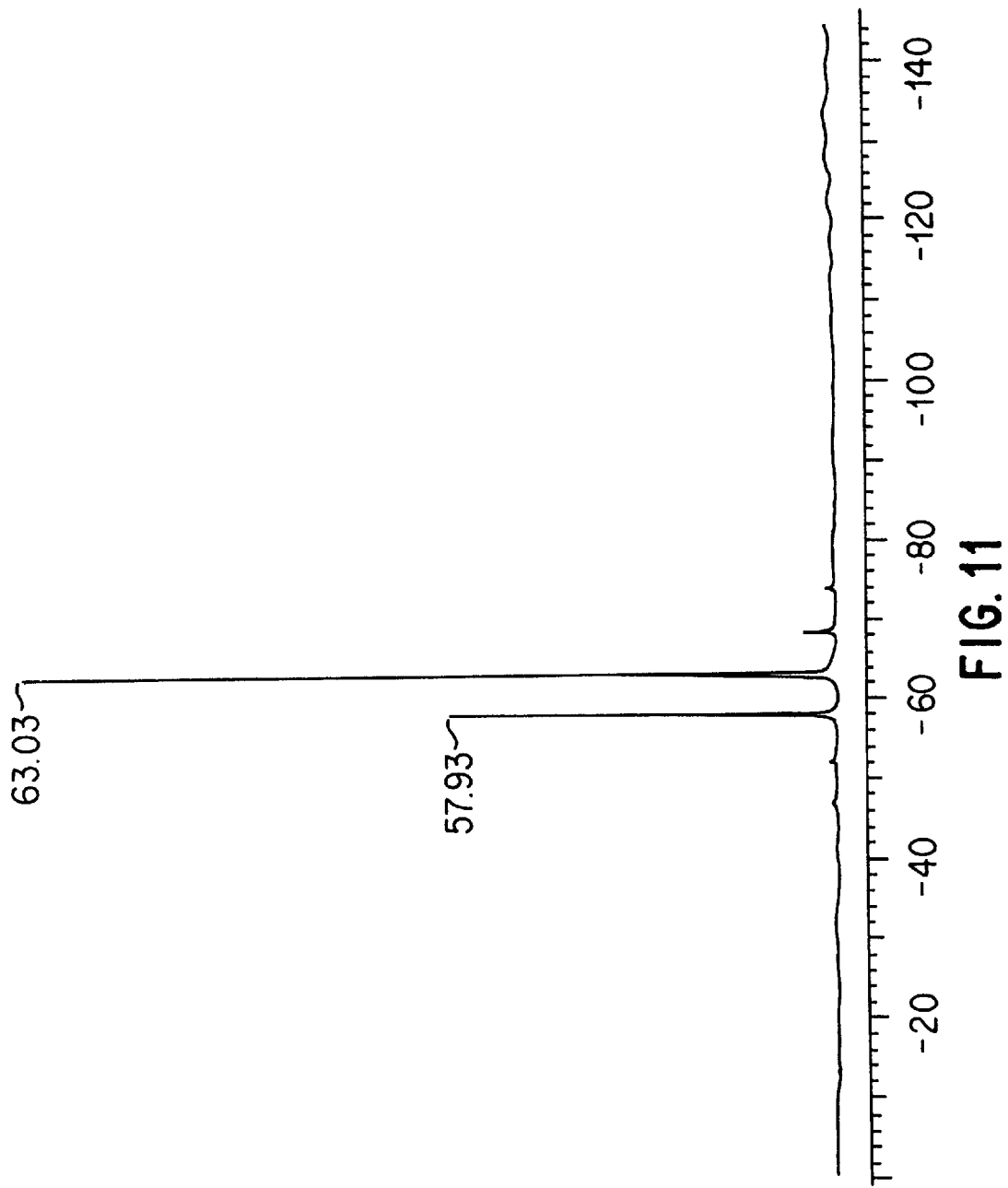
Figure 12:
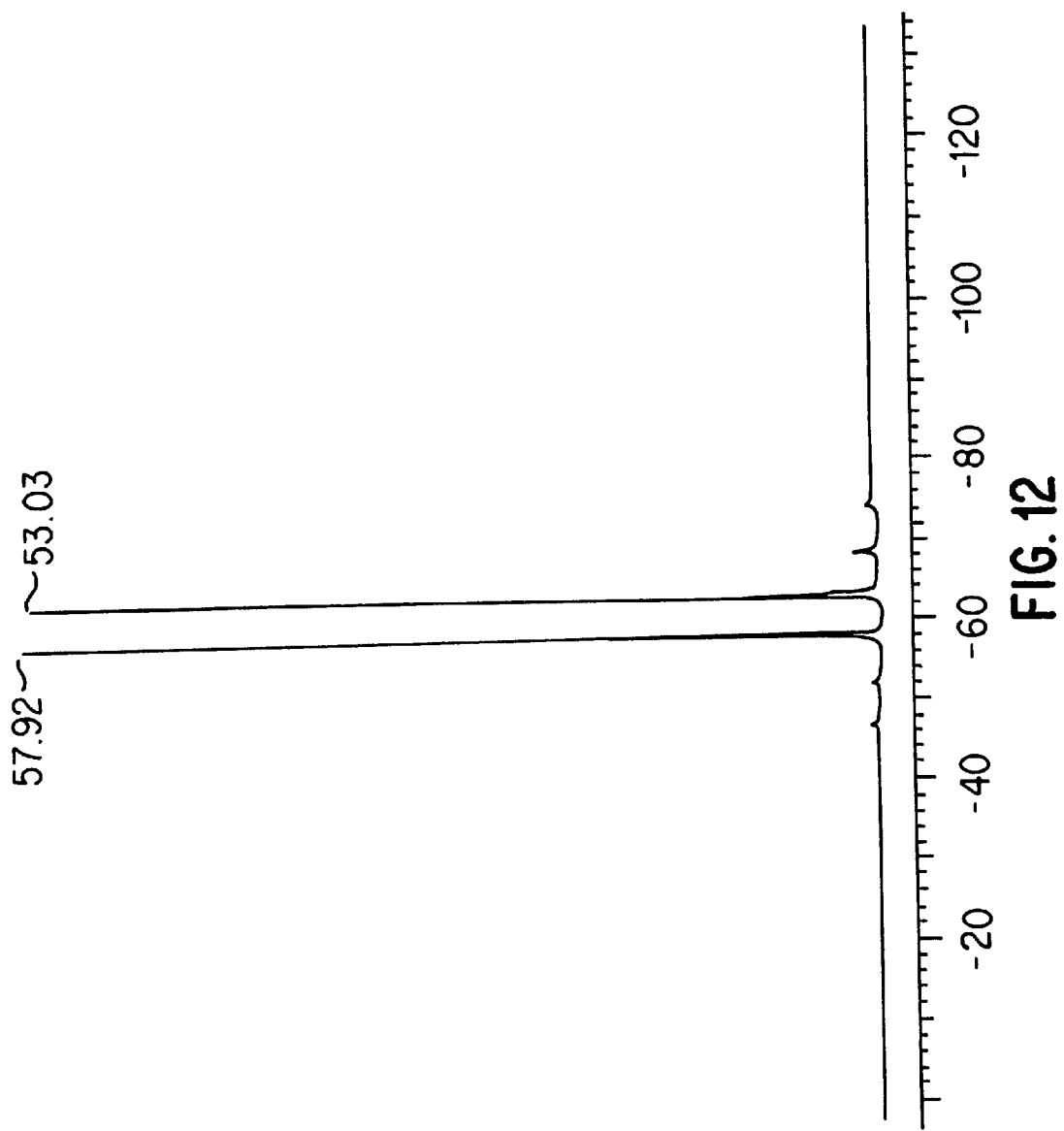
Figure 13:
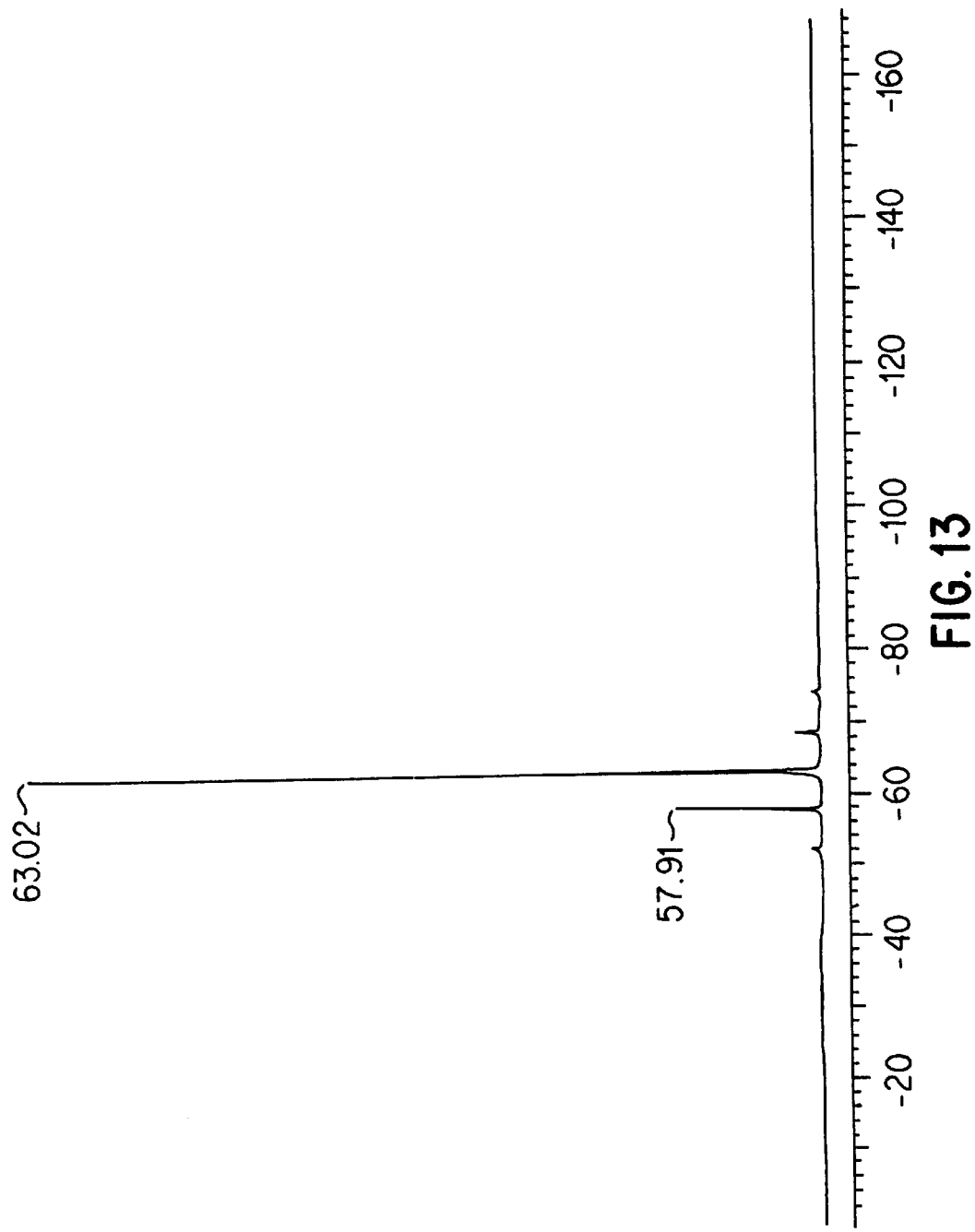

The above methods were used to synthesize additional pools by using different carboxylic acids tags, and using them in combinations and ratios, as discussed in Table 2. FIGS. 4–9 are single bead spectra for Tags 6, 9, 1/7, 2/7, 4/7 and 2/4/7, respectively. FIG. 10 illustrates a multi-bead spectrum for Tag 29. FIG. 11 is a multi-bead spectrum for a one to one ratio of Tag 3 (−63 ppm) to Tag 4 (−58 ppm). Note that Tag 3 attaches 2–3 fold more readily to the bead than Tag 4. FIG. 12 shows a one to three ratio of Tag 3 to Tag 4. FIG. 13 shows a two to one ratio of Tag 3 to Tag 4. Note the higher signal to noise ratio for the multi-bead cases (FIGS. 10–13).

BOC Deprotection

About 3 ml. of a 50% solution of trifluoroacetic acid in dichloromethane was added to each of the above pools of tagged resin. The suspensions were rotated at room temperature for 30 min, and drained. The procedure was repeated. After draining, the resin in each pool was washed with five portions of about 3-ml. dichloromethane, five portions of about 3-ml. 5% diisopropylethylamine in dichloromethane and five portions of about 3-ml. dichloromethane. Then the resin was dried in vacuo. The coded bead is now ready for attachment of the desired library linker, core and first unit of the combinatorial library.

Example 2

Synthesizing and Decoding a Tagged Combinatorial Library

General

The synthetic reactions were performed in 8 ml. reaction vessels on an Argonaut Nautilus 2400 multiple organic synthesizer. Washes were performed using the fast wash syringe pump cycle, and resulted in about 10 minute incubations for each solvent wash. Fmoc Amino acid derivatives were used as received from commercial sources, such as ABI. Side-chains are protected as indicated.

Adding Linker (Illustrated by Structure 2)

About 250 mg samples of each of ten tagged and BOC deprotected resins, as prepared in Example 1, were swelled in 2.6 ml. dichloromethane. Then, 1.2 ml. of a 1M 4-(4-hydroxymethylphenoxy)butyric acid solution (210 mg/ml. in 1:1 dichloromethane:THF) was added, followed by 1.2 ml. of a 1M EEDQ solution (247 mg/ml. dichloromethane). The reactions were incubated at 25 ° C. for 18 h, then drained and washed with dichloromethane (3×4.6 ml.), methanol (2×4.6 ml.), DMF (3×4.6 ml.), methanol (2×4.6 ml.), THF (3×4.6 ml.), 1:1 1N sodium hydroxide:dioxane (2×4.6 ml.), THF (3×4.6 ml.), and ethyl ether (2×4.6 ml.), then dried in vacuo.

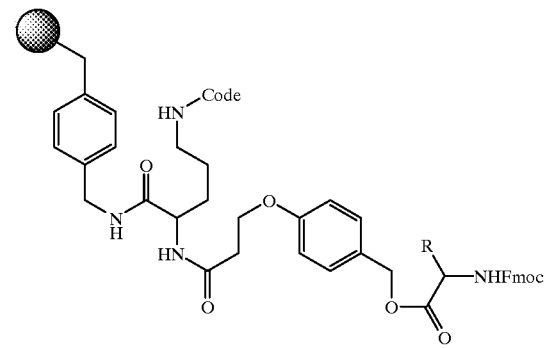

First Diversity Step

Each pool of beads was washed with dichloromethane (1×4.6 ml.). Then, 2 ml. of a 0.5 mM solution of the amino acids was added to each vessel in accordance with the Amino Acid Table. The vessels were cooled to 0° C and 0.4 ml. of a 0.25 M 4-dimethylarminopyridine solution (31 mg/ml. in dichloromethane) chased with 0.8 ml. of a diisopropylcarbodiimide solution (0.195 ml./ml. in dichloromethane) was added to each vessel. After 1 hr, the reactions were allowed to warm to 25° C., incubated for 3 hrs, drained, and the loading repeated, incubating for 7 hrs at 25° C. the second time. The vessels were emptied, washed with DMF (3×4.6 ml.), methanol (2×4.6 ml.), dichloromethane (3×4.6 ml.), methanol (2×4.6 ml.), THF (3×4.6 ml.), and ethyl ether (2×4.6 ml.), then dried in vacuo to obtain a coded bead with a linker and an amino acid that corresponds to the code. Loadings ranged from 0.23–0.46 mmol/g. The two lowest loadings were redone manually by the same procedure to give the final results in the Amino Acid Table.

Amino Acid Table

| Code | Amino Acid, R—CH-(NHFmoc)-COOH | Loading |
|---|---|---|
| 1 | Val | 0.37 |
| 2 | Glu(Boc) | 0.39 |
| 3 | Leu | 0.46 |
| 4 | Phe | 0.38 |
| 5 | Gln(Trt) | 0.33 |
| 6 | Thr(t-Bu) | 0.37 |
| 7 | Tyr(t-Bu) | 0.38 |
| 8 | Lys(Boc) | 0.30 |
| 9 | Trp(Boc) | 0.39 |
| 10 | Ala | 0.33 |

First Mix and Split

A 210 mg sample from each of the tagged resin pools was added to a filter vessel, suspended in dichloromethane, mixed for about 1 hr. washed with ethyl ether (2×40 ml.), and dried. This results in a mixture consisting of a statistical distribution of the ten amino acid attached beads. Approximately 180 ing samples of the mixture were weighed into ten 8 ml. reaction vessels.

Second Diversity Step

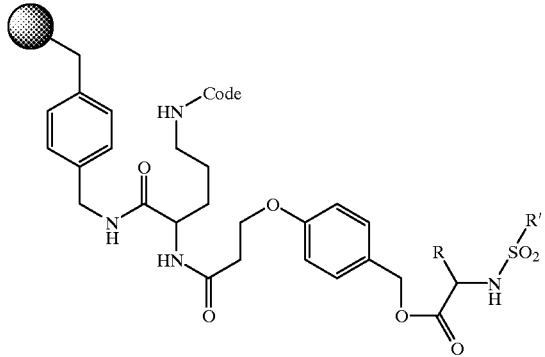

The resins were Fmoc deprotected with piperidine (2×4.6 ml.×30 min incubation), drained, and washed with DMF (3×4.6 ml.), methanol (2×4.6 ml.) and dichloromethane (4×4.6 ml.). Approximately 1.6 ml. of 2M diisopropylethylamine in dichloromethane was added to each vessel, followed by 2 ml. of a 0.55 M solution of the sulfonyl chlorides in dichloromethane in accordance with the Sulfonyl Chloride Table. The reactions were incubated for 12 h at 25° C. The resins were washed with dichloromethane (2×4.6 ml.), methanol (2×4.6 ml.), DMF (3×4.6 ml.), methanol (2×4.6 ml.), dichloromethane (3×4.6 ml.), THF (3×4.6 ml.), and ethyl ether (2×4.6 ml.), then dried in vacuo. A 15 mg sample of each reaction was removed and archived.

Sulfonyl Chloride Table

| Reaction | Sulfonyl Chloride, R'—SO2—Cl |
|---|---|
| 1 | 8-Quinoline |
| 2 | alpha toluyl |
| 3 | Methane |
| 4 | Isopropyl |
| 5 | Trifluoroethane |
| 6 | Dansyl |
| 7 | Butane |
| 8 | Camphor |
| 9 | 2-Thiophene |
| 10 | 3-Trifluoromethylphenyl |

Second Mix and Split

The non-archived resins from the second diversity step were mixed in a filter vessel, suspended in dichloromethane, mixed for 2 hrs, washed with methanol (2×40 ml.), ethyl ether (2×40 ml.), and dried. This results in a statistically distributed mixture of 100 amino acid/sulfonamide attached beads. Approximately 100 mg samples were weighed into ten 8 ml. reaction vessels.

Third Diversity Step

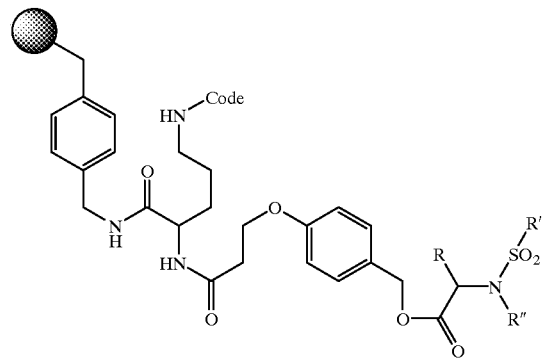

About 500 mg powdered anhydrous potassium carbonate (deprotonates sulfonamide hydrogen) and 4 ml. of a 0.25 M of the alkyl bromides shown in the Alkyl Bromide Table solution in NMP were added to each reaction vessel from the second mix and split step. The reactions were incubated at 25° C. for 48 hrs, washed with 1:1 DMF:water (1×4.6 ml.), water (2×4.6 ml.), DMF (4×4.6 ml.), methanol (2×4.6 ml.), dichloromethane (3×4.6 ml.), methanol (2×4.6 ml.), THF (3×4.6 ml.), and ethyl ether (2×4.6 ml.), then dried under vacuum. The alkylation was driven to completion by adding about 3 ml. of a 0.33 M solution of the alkyl bromides to each tube, cooling to 4° C., and adding 1.2 ml. of a 1M DBU solution in NMP. After 48 hrs at 25° C., the resins were washed by the same procedure as the first alkylation and dried under vacuum.

Alkyl Bromide Table

| Final Pool | Alkyl Bromide, R''-Br |
|---|---|
| 1 | Ethyl |
| 2 | t-Butylacetyl |
| 3 | Tetrahydrofurfuryl |
| 4 | Decyl |
| 5 | α-(4-diethylamino)acetophenonyl |

-continued

Alkyl Bromide Table

| Final Pool | Alkyl Bromide, R"-Br |
|---|---|
| 6 | Allyl |
| 7 | 3-Chlorobenzyl |
| 8 | Methylcyclohexyl |
| 9 | 2-Phenylethyl |
| 10 | 6-Hexanol |

Library "Screening"

Note that the three diversity steps were tagged only once with the fluorine tags—at the first step. In this case, one can decode the compound on each bead with the following analysis. Because one need not mix and split the product of the last diversity step, attachment of the alkyl bromide, one knows exactly which alkyl bromide was reacted with a particular pool of beads. Next, one can use the FNMR to determine which monomer was added on the particular bead. Knowing the first and the third units, the sulfonyl chloride units are sufficiently different to allow for mass spectroscopy analysis.

Furthermore, judicious selection of a diversity monomer can allow for other types of combination analysis. For example, the dansylsulfonamide made by reacting the amino acid with dansyl choloride fluoresces under UV light. Accordingly, when a small portion of pool 6 were placed under a long wave UV lamp, one was able to choose the beads that fluoresced bright green. Thus, the compound that is attached to each of the selected beads must contain the allyl moiety (as determined by Pool 6) and the dansylsulfonamide (as determined by the UV fluorescence). Therefore, one only needs to conduct a FNMR analysis to ascertain which amino acid is attached. Similarly, judicious selection of monomers that contains acetylenes or nitriles can result in a decoding analysis which combines FNMR and IR/Raman spectroscopy.

Example 3

Making Coded Resin by Friedel-Crafts Acylation Trifluoromethylbenzophenone Resin (Scheme 4, Tag 3)

Figure 14:
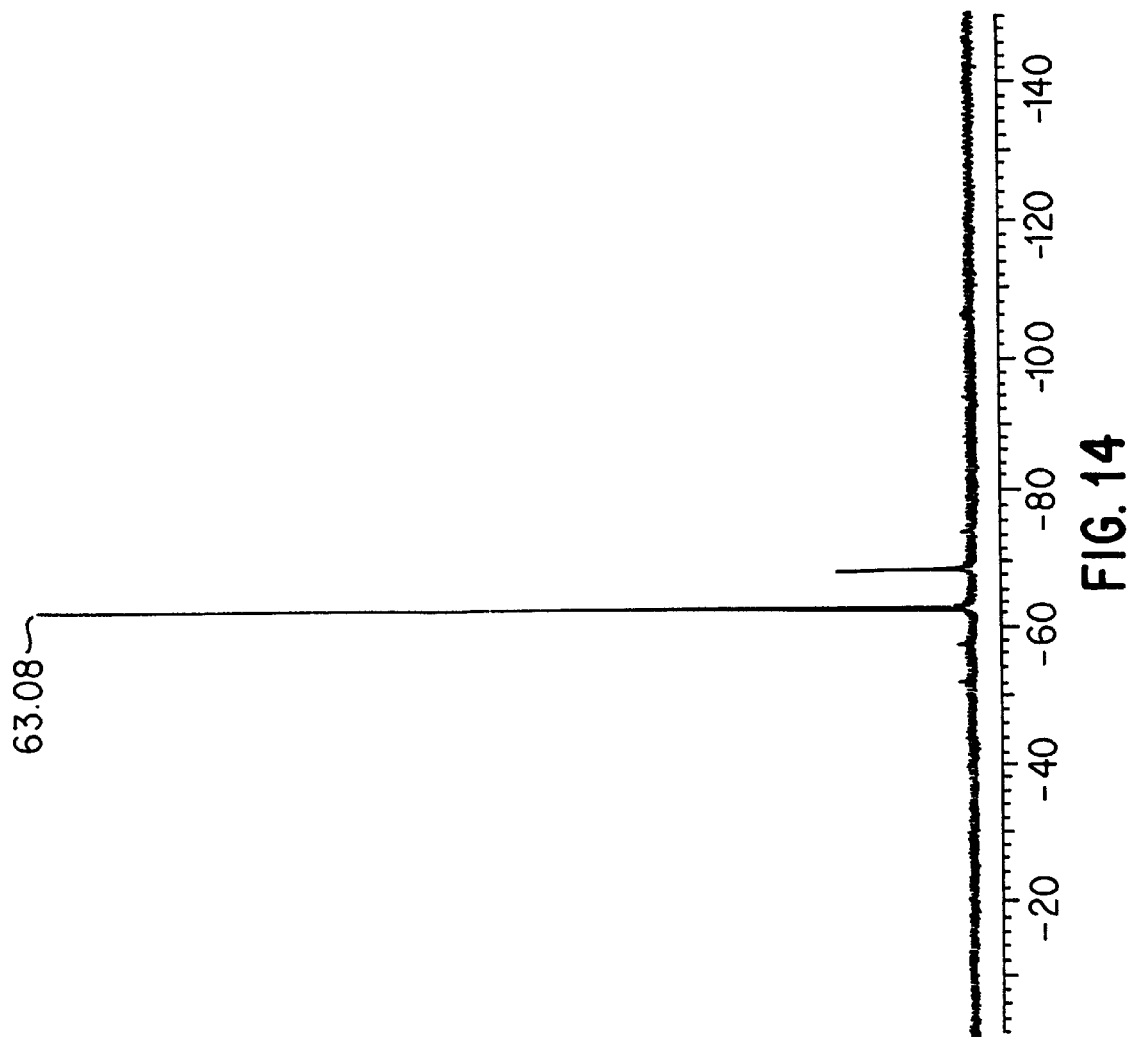

A 500 ml. flask was fitted with an overhead stirrer and charged with about 11.1 g 1% crosslinked polystyrene, about 150 ml. of dichloromethane and about 1.0 g iron(III) chloride. In one portion, 4-trifluoromethylbenzoyl chloride (5.0 g, 24 mmol) was added, and the reaction was stirred for about 18 hrs. The resin was collected, washed with dioxane (3×150 ml.), 1:1 dioxane:2 N hydrochloric acid (3×150 ml.), dioxane (3×150 ml.), methanol (3×150 ml.), and then dried under vacuum to give 12.4 g resin. Elemental analysis indicated that approximately 0.74 mmol $CF_3$ was loaded per gram of resin product. As shown in FIG. 14, the chemical shift for the Friedel-Crafts attachment of Tag 3, was not substatially different than the amide attached Tag 3 (see FIGS. 11–13).

Trifluoromethylbenzhydrylamine Resin (Leukhart Reaction)

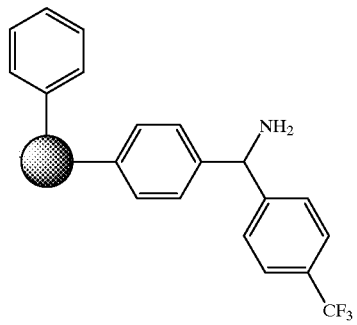

Figure 15:
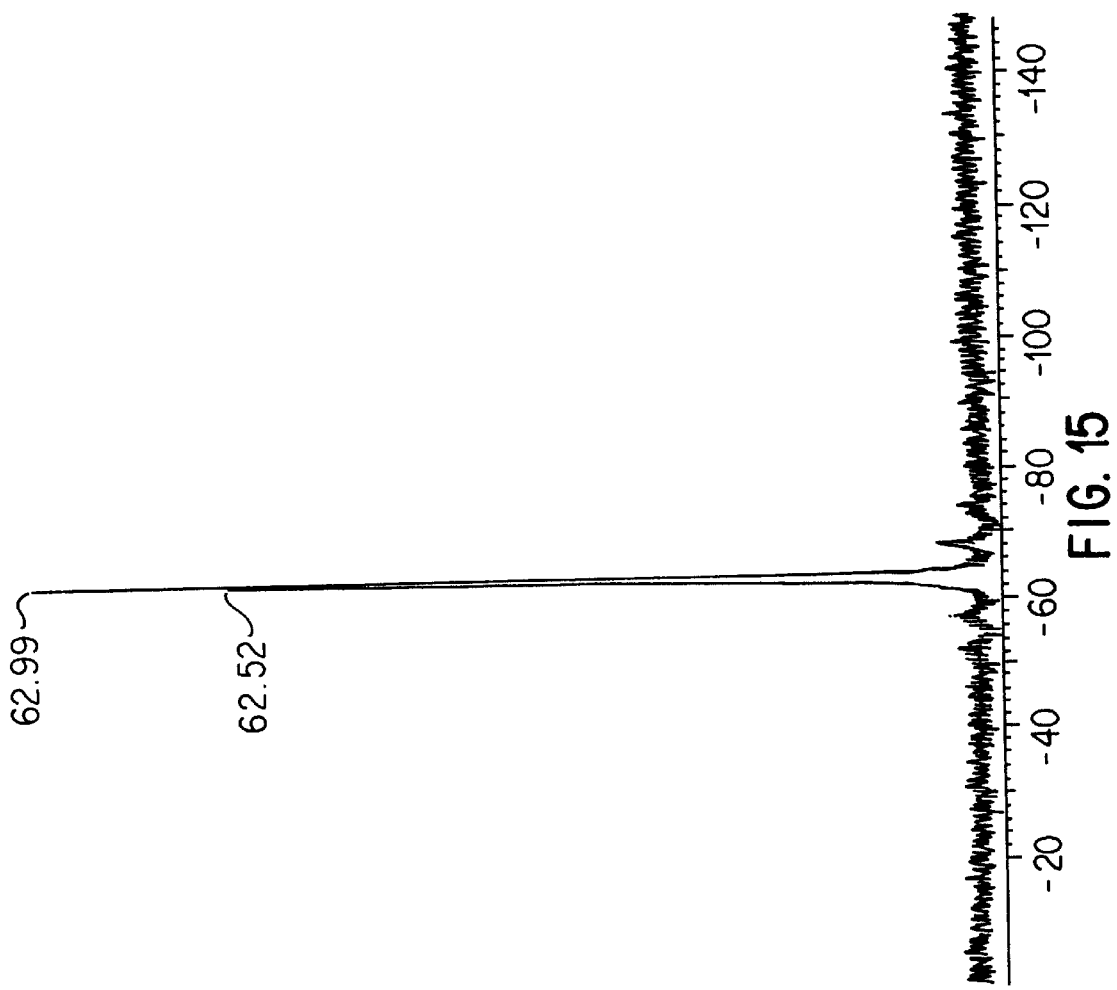

A 250 ml. three neck flask was fitted with an overhead stirrer and a Dean-Stark trap and charged with the above-prepared ketone resin (3.0 g, 2.22 mmol ketone), ammonium formate (10 g, 159 mmol), 88% formic acid (8 ml., 187 mmol), formamide (12 ml., 302 mmol), and 40 ml. of nitrobenzene. The reaction mixture was heated to 165° C., and the distillate collected. After 24 hrs, the resin was collected, washed with ethanol (3×30 ml.), dioxane (3×30 ml.), dichloromethane (3×30 ml.), and ethanol (3×30 ml.). The resin was suspended in 100 ml. 1:1 concentrated hydrochloric acid:ethanol, and heated at reflux for 1 h, collected and washed with ethanol (3×30 ml.), dichloromethane (3×30 ml.), and methanol (3×30 ml.) then dried at 70° C. under vacuum. Elemental indicated that approximately 0.70 mmol $CF_3$ and approximately 0.64 mmol N were loaded per gram of resin product. As shown by a FNMR spectrum of the partially completed reaction (FIG. 15), the fluorine chemical shift changes slightly (approximately 0.5 ppm) when the ketone is transforned to the benzhydrylamine.

Example 4

Synthesis of Iodopolystyrene

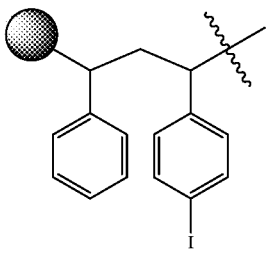

Chromium trioxide ($CrO_3$, 8.0 grams, 80 mM) was placed in an round-bottom flask under argon atmosphere. Over about 5 minutes, $(CH_3)_3SiCl$ (9.7 ml., 76 mM) was added via syringe, The solution was stirred at about 35 ° C. for about 30 minutes, followed by addition of dichloromethane (200 ml). Then, gas was bubbled vigorously through the suspension. After iodine ($I_2$, 12.2 grams, 48 mM) and polystyrene (10 g, 96 mM) were added in sequence, the suspension was stirred vigorously for 4 hours at ambient temperatures. Thereafter, a solution of saturated sodium bisulfite was slowly added until an orange to green color change was observed in the suspension, and bubbling was no longer observed. The suspension was transferred to a fritted glass filter funnel, and washed sequentially with distilled water, DMF (dimethylformamide), water, 2N HCl, distilled water, DMF, distilled water, methanol, dichloromethane, and methanol (500 ml. portions, about 5 minutes to equilibrate each solvent). The p-iodopolystyrene product was dried and stored under vacuum.

Synthesis of chloromethyliodopolystyrene

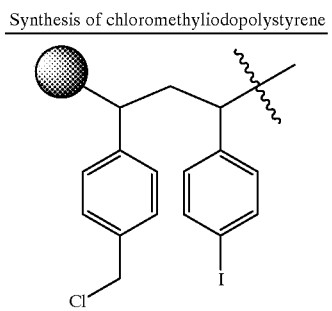

About 5 grams of the p-Iodopolystyrene synthesized above was placed in dichloromethane distilled from CaH$_2$ (200 ml) and allowed to swell for about 1 hour at room temperature. Then, the mixture was brought to about zero degrees in an ice bath under an argon atmosphere. With stirring, chloromethyl methyl ether (10 ml, 130 mM) and SnCl$_4$ 90.5 ml, 4.3 mM) were added slowly via separate syringes to the suspension. Thereafter, the suspension was stirred for about an additional hour at approximately zero degrees under argon atmosphere, then transferred to a fritted filter funnel and washed sequentially with dioxane/distilled water (1:1), dioxane/2 N HCl (1:1), distilled water, dioxane, distilled water, methanol, dichloromethane, and methanol (500 ml portions, about 5 minutes to equilibrate each solvent). Product was dried and stored under vacuum. Elemental analysis of the p-iodo-p-chloromethylpolystyrene product indicated: Cl: 11.61% by weight and I: 24.93% by weight.

Synthesis of Wang Iodopolystyrene

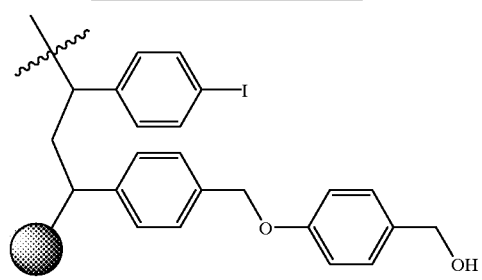

The iodo-chloromethylpolystyrene from above (3.22 grams) was dissolved in 100 ml. DMA and allowed to swell at room temperature for about 30 minutes. About 7.7 grams of 4-hydroxybenzyl alcohol (62 mM) was added to the suspension, followed by sodium methoxide (1.7 g, 31 mM). Then, the reaction mixture was heated to reflux under an argon atmosphere for about 48 hours. At that time, the suspension was allowed to cool to room temperature and transferred to a fritted filter funnel and washed sequentially with dioxane/distilled water (1:1), dioxane/2 N HCl (1:1), distilled water, dioxane, distilled water, DMF, distilled water, DMF, distilled water, methanol, dichloromethane, and methanol (500 ml portions, about 5 minutes to equilibrate each solvent). The product was dried under vacuum and stored.

Synthesis of tagged Wang polystyrene

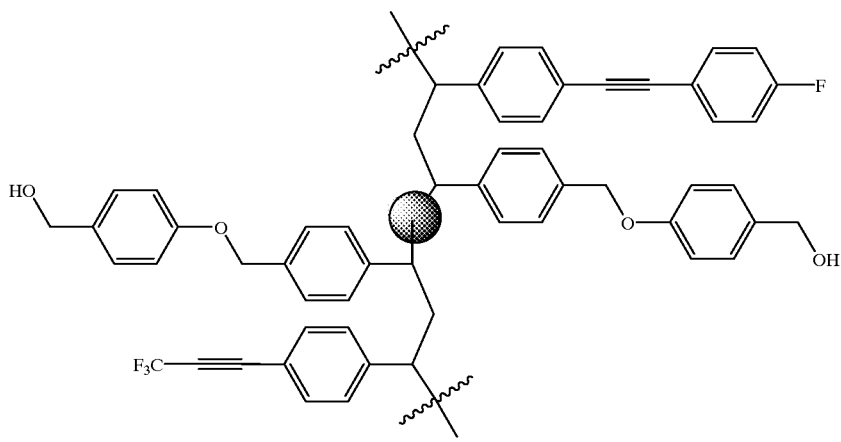

The Wang iodopolystyrene synthesized above (100 mg) was added to a solvent mixture composed of dimethyl formamide/distilled water/triethyl amine (9:1:1) (5 ml. total solvent volume) and allowed to swell for about 30 minutes at room temperature. A premixed solution of DMF (0.5 ml) containing "tags" (for example, 3,3,3-trifluoropropyne and 1-ethynyl-4-fluorobenzene) (50 mg of each) was added to the polymer bead suspension followed by potassium carbonate (50 mg, 0.36 mM), tetrabutylammonium bromide ( 50 mg, 0.16 mM). Then the suspension was stirred under argon for about 30 minutes, at which time tetrakis(triphenyl phosphine)palladium(0) (25 mg, 0.02 mM) was rapidly added. The reaction mixture was heated to 80° C. and agitated at that temperature under an argon atmosphere for 16 hours. Thereafter, the mixture was allowed to cool to room temperature, whereupon a saturated solution of ammonium acetate (5 ml )was added, and the mixture agitated at room temperature for about 30 minutes. At that time, dimethoxyethane (5 ml) was added, and the mixture agitated for an additional 30 minutes. Then the mixture was transferred to a fritted filter funnel and washed sequentially with distilled water, dimethyl formamide, distilled water, 2 N HCl, distilled water, dimethyl formamide, distilled water, methanol, dichloromethane and methanol (50 ml portions, about 10 minutes between washes to equilibrate). The mixture of two tags is used create a code.

We claim:

1. A process of coding individual members of a combinatorial chemical library synthesized on a plurality of solid supports comprising covalently attaching at least one FNMR readable tag to each of the plurality of solid supports, wherein the tag is selected from the group consisting of Tags 1–62 and combinations thereof.

2. The process of claim 1 wherein the tag is selected from the group consisting of Tags 1–35 and combinations thereof.

3. The process of claim 1 wherein fluorine-containing carboxylic acid tags selected from tags 1–57 are attached to one or more of the alpha and epsilon amino positions of a lysine linker.

* * * * *